United States Patent
Takashima et al.

(10) Patent No.: US 6,528,230 B1
(45) Date of Patent: Mar. 4, 2003

(54) DYE PRECURSOR, IMAGE FORMING MATERIAL, AND IMAGE FORMING METHOD

(75) Inventors: Masanobu Takashima, Shizuoka-ken (JP); Hiroshi Sato, Shizuoka-ken (JP); Hirotaka Matsumoto, Shizuoka-ken (JP); Yuuichi Fukushige, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/493,111

(22) Filed: Jan. 28, 2000

(30) Foreign Application Priority Data

Jan. 28, 1999 (JP) ............................................. 11-020091

(51) Int. Cl.$^7$ ........................ G03F 7/004; G03F 7/029; C09B 57/00

(52) U.S. Cl. ................. 430/211; 430/270.1; 430/281.1; 430/955; 430/222; 564/123; 564/139

(58) Field of Search .................................. 430/138, 200, 430/203, 211, 222, 348, 955, 270.1, 281.1; 564/92, 123, 139, 82, 99

(56) References Cited

U.S. PATENT DOCUMENTS

| | | | |
|---|---|---|---|
| 4,373,017 A | * 2/1983 | Masukawa et al. | 430/270.1 |
| 4,902,604 A | * 2/1990 | Yamaguchi et al. | 430/281 |
| 5,045,427 A | * 9/1991 | Hara | 430/138 |
| 5,236,884 A | 8/1993 | Boggs et al. | 503/201 |
| 5,252,425 A | * 10/1993 | Bagchi | 430/201 |
| 5,350,870 A | 9/1994 | Boggs et al. | 560/27 |
| 5,432,041 A | 7/1995 | Biavasco et al. | 430/203 |
| 5,492,805 A | * 2/1996 | Krepski et al. | 430/619 |
| 5,563,017 A | * 10/1996 | Yabuki et al. | 430/138 |
| 5,696,289 A | * 12/1997 | Krepski et al. | 564/41 |

FOREIGN PATENT DOCUMENTS

| | | | | |
|---|---|---|---|---|
| EP | 035262 A2 | * 9/1981 | ............ | G03C/1/72 |
| EP | 689683 B1 | * 6/1997 | | |
| JP | 357045537 A | * 3/1982 | ............ | G03C/1/72 |
| JP | 403072341 A | * 3/1991 | ............ | G03C/1/06 |
| JP | 5-204087 | 8/1993 | ........... | G03C/1/498 |
| JP | 8-507885 | 8/1996 | ............ | G03C/8/40 |
| JP | 409263581 A | * 10/1997 | ......... | C07D/233/88 |
| JP | 10-502460 | 3/1998 | ............ | G03C/8/40 |

* cited by examiner

Primary Examiner—Janet Baxter
Assistant Examiner—Yvette C. Thornton
(74) Attorney, Agent, or Firm—Sughrue Mion, PLLC

(57) ABSTRACT

The present invention provides a dye precursor for forming color through contact with a base and which is represented by either of the following formulas (1) and (2):

$$\text{Ar} - \underset{\underset{L}{|}}{N} - \text{Cp} \quad (1)$$

$$\text{Ar} - \underset{\underset{L}{|}}{\overset{\overset{L_2}{|}}{N}} - \text{Cp} \quad (2)$$

wherein Ar represents an aromatic ring or a heterocyclic ring, each of which may have a substituent; Cp represents a coupler residue; $L_1$ represents a protective group which can be eliminated by a base; and $L_2$ represents an elimination group or a protective group which is eliminated after $L_1$ is eliminated. Further, the present invention provides an image forming material and an image forming method, wherein the image forming material has an image forming layer on a support, the image forming layer containing at least one type of each of a photopolymerization initiator, a dye precursor which can form color through contact with a base, a base or a base precursor, and a polymerizable compound.

10 Claims, 1 Drawing Sheet

F I G. 1
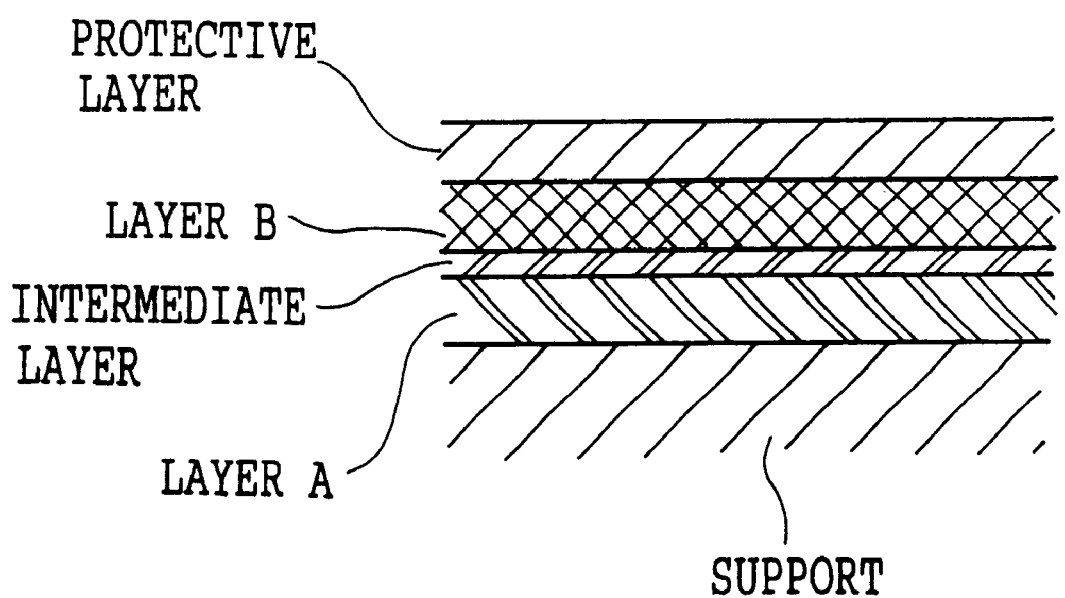

DYE PRECURSOR, IMAGE FORMING MATERIAL, AND IMAGE FORMING METHOD

BACKGROUND OF THE INVENTION

1. Field of the Invention

The present invention relates to dye precursors as novel compounds which act effectively.

Further, the present invention relates to a monocolor or multicolor image forming material which is used for various light sources emitting light having wavelengths from UV to near-infrared rays, and an image forming method using the same, and more particularly to an image forming material which is excellent in sensitivity, light-fastness of image, hues in image areas, and whiteness at non-image areas, and an image forming method using the same.

2. Description of the Related Art

Heretobefore, various types of dry type image forming methods which do not use liquid type developers and the like, and which do not produce waste materials have been researched. Among these, methods in which a composition to be hardened with light are used as components in an image forming layer of a recording material (image forming material) are attracting notice.

This method is characterized in that the composition to be hardened with light contained in the image forming layer are hardened through an exposure process so that a latent image is formed, while components, which are contained in unexposed portions of the image forming layer and which contribute to a color-forming reaction, are heated and/or pressurized so as to move inside the image forming layer so that an image produced through color formation is formed. In a case of using a recording material in such a method as described above, first of all, light is transmitted, through an image original, to expose a recording material, and then the exposed portion is hardened so that a latent image is formed. Thereafter, this recording material is heated or pressurized so as to move the components which are contained in unhardened portions (unexposed portions) of the layer and which participate in a color-forming reaction, thus forming a visible image.

As an example of such a recording material as described above, a recording material disclosed in Japanese Patent Application Laid-Open (JP-A) No. 61-123838 is known. Namely, the recording material is formed by laminating a layer which contains therein photopolymerization components formed of a vinyl monomer having acidic groups and photopolymerization initiators; an isolation layer; and a layer which is formed by electron donative colorless dyes. In a case of this recording material, the acidic groups do not diffuse under heat at non-image areas, namely, in portions which are hardened through a photopolymerization reaction, and thus problems in which non-image areas become colored do not occur. However, problems have arisen in that image density is low and light-fastness is low.

Examples of recording materials in which image density is improved are disclosed in JP-A Nos. 3-87827 and 4-211252. The former is a recording material which has an image forming layer in which one of two components of a two-component type photosensitive and heat-sensitive color-forming recording material is contained in microcapsules, and the other is contained in portions outside the microcapsules of the image forming layer (1) as hardening compounds of photo-curing type composition, or (2) together with the photo-curing type composition. The latter is a photosensitive and heat-sensitive recording material which comprises a support, and a layer applied on the support, the layer including: microcapsules which contain electron donative colorless dyes; and outside of the microcapsules, a photo-curing type composition which contains electron acceptive compounds, polymerizable vinyl monomers, and photopolymerization initiators. However, since both of the examples use electron donative colorless dyes which are so-called phthalide compounds, as dye precursors, a satisfactory level of light-fastness is not attained in the images.

In a similar manner to the above description, as an example of a photosensitive and pressure-sensitive paper, recording materials disclosed in Japanese Patent Publication (JP-B) Nos. 64-7378, 64-7377, and 64-7376 are known. However, since dye precursors used in these recording materials are also phthalide compounds, a sufficient level of light-fastness is not attained in the images of recording materials of these examples.

A heat-type image forming method is disclosed in JP-B No. 5-42359. The heat-type image forming method is such that a recording material, which has an image forming layer containing compounds which have carbamate portions that are instable under heat and which cause irreversible monomolecular division, is heated imagewise, and the compounds decompose with heating so as to form a visible image. In this method, dye precursors other than phthalide compounds can be used. However, since the dye precursors form color by heating alone, a large amount of heat must be used when images are written, thus causing problems such as requiring a large-size image forming apparatus and delaying a processing rate. Further, there has been a problem in that non-image areas become fogged by remaining or accumulated heat during image writing. Since color-formation is controlled by heating alone, even in terms of storage stability over time, there has been a problem in that the non-image areas tend to become fogged.

Japanese Patent No. 2744101 discloses a heat-sensitive element. In the heat-sensitive element, dye precursors which are substituted by protective groups which are thermally eliminable when heated and by elimination groups which are eliminated irreversibly when heated are heated imagewisely so that images are formed. Also in this case, since color formation is controlled by heating alone, there has been almost the same problem as in the heat-type image forming method which is disclosed in the aforementioned JP-B No. 5-42359. Further, because images produced through color formation are not fixed in the image forming layer, there have been problems with storage stability over time. For example, when heat is applied to the heat-sensitive element having an image thereon, there has been a problem in that dye precursors in non-image areas of the image forming layer decompose gradually, which leads to fogging.

Namely, it is desired to provide dye precursors which form color due to elements other than heating, or through action of another element in combination with heating.

Various types of photosensitive and heat-sensitive photographic materials using dye precursors are disclosed in JP-A No. 5-204087, and in Japanese Patent Application National Publication (Laid-Open) Nos. 8-507885 and 10-502460. However, since silver halides are used as photosensitive materials, from the viewpoint of storage stability and handling, they are not suitable. Therefore, it has been desired to obtain an image forming material capable of forming an image through a completely dry processing system in which silver halides are not used (which will be referred to as 'non-silver salt', hereinafter).

SUMMARY OF THE INVENTION

It is an object of the present invention to provide dye precursors which are novel compounds having the characteristic of forming color due to elements other than heating, or through action of another element in combination with heating.

Further, it is another object of the present invention to provide a monocolor or a multicolor non-silver salt type image forming material and an image forming method using the same, wherein various light sources emitting light of wavelengths of each range from UV to near-infrared rays can be used in a full-dry processing system in which use of developing solutions is not needed, and which does not produce waste materials, and wherein images which are excellent in sensitivity, image quality, and light-fastness can be formed.

Further, the above-described objectives can be accomplished by the present invention which will be described hereinafter. Namely, a first aspect of the present invention is to provide dye precursors as novel compounds. Specific examples of these dye precursors include two types of dye precursors as follows.

(Dye Precursor A)

A dye precursor for forming color through contact with base, and which is represented by the following formula (1):
Formula (1):

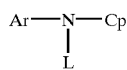

(1)

wherein Ar represents an aromatic ring or a heterocyclic ring, each of which may have a substituent; Cp represents a coupler residue; and L represents a protective group which can be eliminated by a base.

(Dye Precursor B)

A dye precursor for forming color through contact with a base, and which is represented by the following formula (2):
Formula (2):

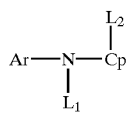

(2)

wherein Ar represents an aromatic ring or a heterocyclic ring, each of which may have a substituent; Cp represents a coupler residue; $L_1$ represents a protective group which can be eliminated by a base; and $L_2$ represents an elimination group or a protective group which is eliminated after $L_1$ is eliminated.

Each of these dye precursors can form color by having a base act upon the dye precursor at room temperature or within a range of temperature at which it is impossible for the dye precursor to form color without a base even if the dye precursor is heated. By using these dye precursors in an image forming layer of an image forming material, an image forming material which can exhibit excellent color formation with a small amount of energy and images with extremely excellent storage stability can be obtained.

A second aspect of the present invention relates to an image forming material and an image forming method using the same, and more particularly to an image forming material comprising an image forming layer and a support, the image forming layer being disposed on the support and containing at least one type of each of a photopolymerization initiator, a dye precursor which can form color through contact with a base, a base or a base precursor, and a polymerizable compound.

According to the second aspect of the present invention, the image forming material has high photo-sensitivity although it is a non-silver salt image forming material, and can provide an image which is excellent in hues and light-fastness. Further, the obtained image can be fixed as an image with excellent light-fastness by polymerizing both image portions and background portions (non-image areas). The image forming material is irradiated with light imagewisely, the polymerizable compound is polymerized by radicals which generate at light-irradiated portions from a radical generating agent. Accordingly, the light-irradiated portions are hardened, and the base or base precursors in vicinities of the light-irradiated portions are fixed in their respective positions so that a latent image is formed (latent image forming process). Thereafter, the entire surface of the image forming layer is heated and/or pressurized so that a color-formed image is formed in accordance with the latent image (developing process). As a result, an image forming method which is excellent in terms of sensitivity and high processing speed, which does not use developing solutions and which does not produce waste material, can be provided. The entire surface of the image forming layer is irradiated with light as needed and images are fixed on the layer (fixation process) so that images with superior light-fastness can be formed.

In the second aspect of the present invention, since the dye precursor which can form color through contact with a base is used, in contrast to an image forming material which uses dye precursors which form color by heating alone, the image forming material of the present invention is characterized in that non-image areas are not likely to be fogged. By setting the temperature at which the entire surface of the image forming layer is heated to a temperature at which it is impossible for the dye precursor to form color without a base even if the dye precursor is heated, a non-image area does not become fogged even when the entire surface of the image forming layer is heated.

BRIEF DESCRIPTION OF THE DRAWINGS

FIG. 1 is an enlarged cross-sectional view of an image forming material prepared in examples of the present invention.

DESCRIPTION OF THE PREFERRED EMBODIMENTS

First Embodiment of the Present Invention

A dye precursor according to a first embodiment of the present invention will be explained. The dye precursor of the first embodiment of the present invention can form color through contact with a base and comprises a dye precursor A represented by the following formula (1) and a dye precursor B represented by the following formula (2).

(Dye Precursor A)

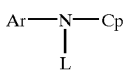
(1)

wherein Ar represents an aromatic ring or a heterocyclic ring, each of which may have a substituent; Cp represents a coupler residue; and L represents a protective group which can be eliminated by a base.

(Dye Precursor B)

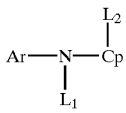
(2)

wherein Ar represents an aromatic ring or a heterocyclic ring, each of which may have a substituent; Cp represents a coupler residue; $L_1$ represents a protective group which can be eliminated by a base; and $L_2$ represents an elimination group or a protective group which is eliminated after $L_1$ is eliminated.

Ar in the aforementioned formulas (1) and (2) include groups represented by the following structural formula (4).

Structural Formula (4):

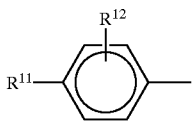
(4)

wherein $R^{11}$ represents $NR^{13}R^{14}$ or $OR^{15}$; $R^{13}$ and $R^{14}$ each represent a hydrogen atom, an alkyl group, and an aryl group; $R^{15}$ represents H, $COR^{16}$, $CO_2R^{16}$, $SO_2R^{16}$, $CONR^{17}R^{18}$, an alkyl group or an aryl group; $R^{16}$ represents an alkyl group, an aryl group, or a heterocyclic group; and $R^{17}$ and $R^{18}$ represents H, an alkyl group, an aryl group, or a heterocyclic group.

Preferable examples of the aforementioned $R^{13}$ and $R^{14}$ include: a hydrogen atom; an alkyl group having 1 to 30 carbon atoms; and an aryl group having 6 to 20 carbon atoms. Specific examples include hydrogen, methyl, ethyl, propyl, butyl, octyl, octadecyl, hydroxyethyl, methanesufonilaminoethyl, phenoxyethyl, cyanoethyl, benzoyloxyethyl, cyclohexyl, phenyl, tolyl, methoxyphenyl, benzyl, and the like.

In $NR^{13}R^{14}$, $R^{13}$ and $R^{14}$ can form a ring which can contain a hetero atom such as O, S, N or the like, and $R^{13}$ or $R^{14}$ can form a ring together with a phenyl ring to which $NR^{13}R^{14}$ is bonded.

Preferable examples of the aforementioned $R^{15}$ include a hydrogen atom, $COR^{16}$, $CO_2R^{16}$, $SO_2R^{16}$, $CONR^{17}R^{18}$, an alkyl group, and an aryl group, each of which has 1 to 40 carbon atoms. Specific examples thereof include a hydrogen atom, methyl, ethyl, octyl, benzyl, phenyl, acetyl, benzoyl, ethoxycarbonyl, phenylsulfonil, dibutylaminocarbonyl, and the like.

In the aforementioned formula (4), preferably, $R^{11}$ is $NR^{13}R^{14}$.

In the aforementioned formula (4), $R^{12}$ represents a hydrogen atom, an alkyl group, an aryl group, an alkoxy group, an aryloxy group, a sulfonylamino group, an acylamino group, an alkoxycarbonyl group, a carbamoyl group, or a sulfamoyl group. Among these, the alkyl group, the alkoxy group, the acylamino group and the hydrogen atom are preferable. Further, preferably, $R^{12}$ is positioned at a meta-position of $R^{11}$ in the aforementioned formula (4).

Preferable examples of Ar in the aforementioned formulas (1) and (2) include pyridine, thiazole, furan, oxazole, pyrimidine, and the like. These examples can contain substituents. Examples of the substituents include an amino group, a dialkylamino group, an alkylamino group, an acylamino group, an alkyl group, an aryl group, an alkoxy group, an alkoxycarbonyl group, a carbamoyl group, a sulfamoyl group, and the like.

The alkyl group contained in the aforementioned Ar can be saturated or unsaturated, or can be cyclic.

The alkyl group, the aryl group, and the heterocyclic group of the present invention can contain substituents. Examples of these substituents include an alkyl group, an aryl group, a hydroxy group, a nitro group, a cyano group, a halogen group, an alkylsulfonyl group, an arylsulfonyl group, an alkoxycarbonyl group, an aryloxycarbonyl group, an acyl group, an amino group, an alkylamino group, a dialkylamino group, an acylamino group, an alkylsulfonylamino group, an arylsulfonylamino group, a carbamoyl group, a sulfamoyl group, an alkylthio group, an arylthio group and a heterocyclic group.

Cp in the aforementioned formula (1) represents a so-called 4-equivalent coupler residue. On the other hand, Cp in the aforementioned formula (2) represents a so-called 4 or 2-equivalent coupler residue. These couplers can be any of known couplers.

Examples of the couplers are described in Research Disclosure No. 17643, VII-C to G, and No. 307105, VII-C to G. However, it is desirable to use non-diffusive couplers having hydrophobic groups which are called ballast groups, or to use polymerized couplers. Among couplers which are preferably used in the present invention, as examples of cyan couplers, there include naphthol-based couplers, phenol-based couplers, and the like. Examples of these cyan couplers are disclosed in U.S. Pat. Nos. 2,369,929, 2,772,162, 2,801,171, 2,895,826, 3,446,622, 3,758,308, 3,772,002, 4,052,212, 4,126,396, 4,146,396, 4,228,233, 4,254,212, 4,296,199, 4,296,200, 4,327,173, 4,333,999, 4,334,011, 4,343,011, 4,427,767, 4,451,559, 4,690,889, and 4,775,616, West German Patent Laid-Open No. 3329729, Europe Patent Nos. 121365A and 249453A, and JP-A No. 61-42658. Examples of magenta couplers include imidazole[1,2-b] pyrazoles described in U.S. Pat. No. 4,500,630, and pyrazolo[1,5-b][1,2,4]triazoles described in U.S. Pat. No. 4,540,654.

Further, examples of a pyrazolo triazole coupler in which a branched alkyl group is directly connected to 2-, 3-, or 6-position of a pyrazolotriazole ring, such as that disclosed in JP-A No. 61-65245; a pyrazoloazole coupler in which a sulfoneamide group is contained in a molecule such as that disclosed in JP-A No. 61-65246; a pyrazoloazole coupler which has an alkoxyphenylsulfonamide ballast group, such as that disclosed in JP-A No. 61-147254; a pyrazolotriazole coupler which has an alkoxy group or an aryloxy group at a 6-position thereof, such as those disclosed in Europe Patent (Laid-Open) Nos. 226849 and 294785. Couplers disclosed in U. S. Pat. Nos. 3,061,432, 3,725,067, 4,310,619, 4.351, 897, and 4556630, Europe Patent No. 73636, JP-A Nos. 55-118034, 60-35730, 60-43659, 60-185951, and 61-72238, International Publication WO No. 88/04795, and Research Disclosure Nos. 24220 and 242306 are also used in the present invention. Examples of yellow couplers are disclosed in U.S. Pat. Nos. 3,933,501, 3,973,968, 4,022,620, 4,248,961, 4,314,023, 4,326,024, 4,401,752, and 4,511,649, European Patent No. 249473A, JP-B No. 58-10739, U. K. Patent Nos. 1425020 and 1476760.

Typical examples of polymerized dye forming couplers are disclosed in U.S. Pat. Nos. 3,451,820, 4,080,211, 4,367,282, 4,409,320, and 4,576,910, European Patent No. 341188A, and U. K. Patent No. 2102137.

Other examples of these couplers are also disclosed in Japanese Patent Application Nos. 9-260336 and 9-271395.

Examples of L in the aforementioned formula (1) and $L_1$ in the aforementioned formula (2) include compounds represented by the following structural formulas (5) to (10).

Structural Formula (5):

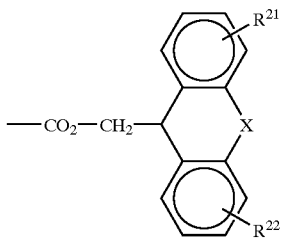

(5)

wherein X represents O, S, $SO_2$, or a single bond; and $R^{21}$ and $R^{22}$ represent a hydrogen atom, an alkyl group, an alkoxy group, an aryl group, or EWG. Further, EWG is an electron attractive group, and more particularly, a substituent having a Hammett's substituent constant σ with a positive value. Examples of these substituents include: a halogen atom, sulfamoyl, sulfonamide, alkoxy, carbonyl, and sulfonyl (the same examples of substituents are applied for the following formulas (6) to (10)).

Structural Formula (6):

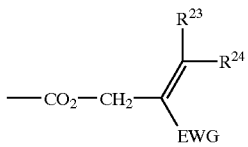

(6)

wherein $R^{23}$ and $R^{24}$ represent a hydrogen atom, an alkyl group, or an aryl group. $R^{24}$ and EWG can form a ring in combination. As an example of the structural formula (6) in which a ring is formed

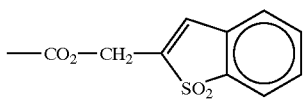

or the like can be listed.

Structural Formula (7):

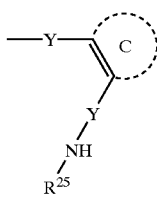

(7)

wherein Y represents CO or $SO_2$, $R^{25}$ represents a hydrogen atom, an alkyl group, an aryl group or a heterocyclic ring, and C represents an aryl group or a heterocyclic group (for example, a phenyl group, a naphthyl group, a pyridyl group, a thienyl group, or a pyrrole group).

Structural Formula (8):

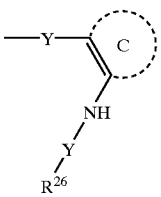

wherein Y represents CO or $SO_2$, and $R^{26}$ is the same as $R^{25}$ in the structural formula (7).

Structural Formula (9):

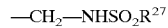

wherein $R^{27}$ is the same as $R^{25}$ in the structural formula (7).

Structural Formula (10):

wherein

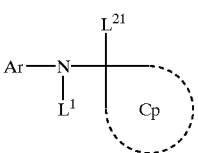

represents an aryl group whose heterocyclic ring is condensed. As an example of the structural formula (10),

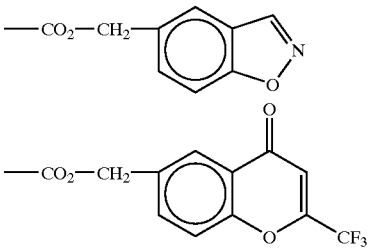

can be listed.

In a case in which Cp in the aforementioned formula (2) is 2-equivalent coupler residue, the formula (2) is represented by the following formula (2-1).

Formula (2-1):

$$Ar-N(L^1)-L^{21}\cdots Cp$$

wherein $L^{21}$ is an elimination group which is eliminated after $L^1$ is eliminated; and

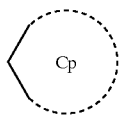

is 2-equivalent residue of Cp.
Examples of $L^{21}$ are listed below.

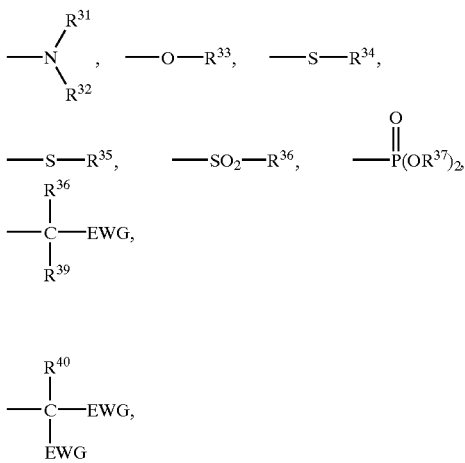

halogen atom
wherein each of $R^{31}$, $R^{32}$, $R^{33}$ and $R^{34}$ independently represent a hydrogen atom, an alkyl group, an aryl group, an acyl group, an alkylsulfonyl group, an arylsulfonyl group, an alkyloxycarbonyl group, an aryloxycarbonyl group, or an amide group. $R^{31}$ and $R^{32}$ in combination can form a ring structure which can be saturated or unsaturated in this case. Further, each of $R^{35}$, $R^{36}$, $R^{37}$, $R^{38}$, and $R^{39}$ independently represents a hydrogen atom, an alkyl group or an aryl group. $R^{40}$ represent a hydrogen atom, an alkyl group, an aryl group, a halogen atom or EWG.

In a case in which Cp in the aforementioned formula (2) is 4-equivalent coupler residue, the formula (2) is represented by a following formula (2—2).

Formula (2—2):

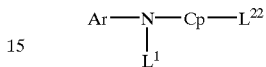

wherein $L^{22}$ represents a protective group which is eliminated after $L^1$ is eliminated, and Cp represents 4-equivalent coupler residue.

Specific examples of $L^{22}$ include protective groups of a nitrogen atom and an oxygen atom, such as an acyl group, an alkylsufonyl group, an arylsulfonyl, a formyl group, and an alkyloxycarbonyl group.

Below, specific examples of the dye precursor A represented by the aforementioned formula (1) (1, 3, 7, 8, 12, 14, 15, 16, 18, 19, 20, 21, 23, 26, 27, and 28 in the specific examples described below) and the dye precursor B represented by the aforementioned formula (2) (2, 4, 5, 6, 9, 10, 11, 13, 17, 22, 24, and 25 in the specific examples described below) are shown.

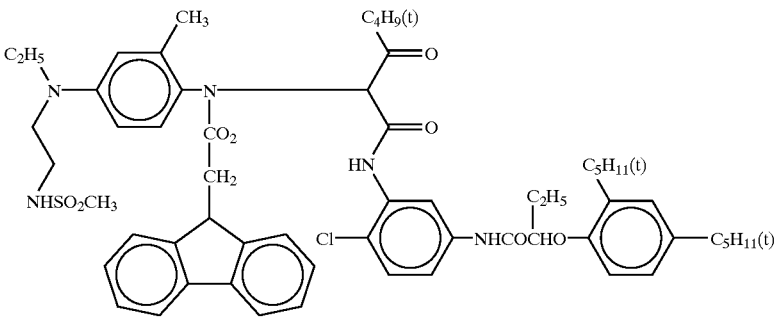

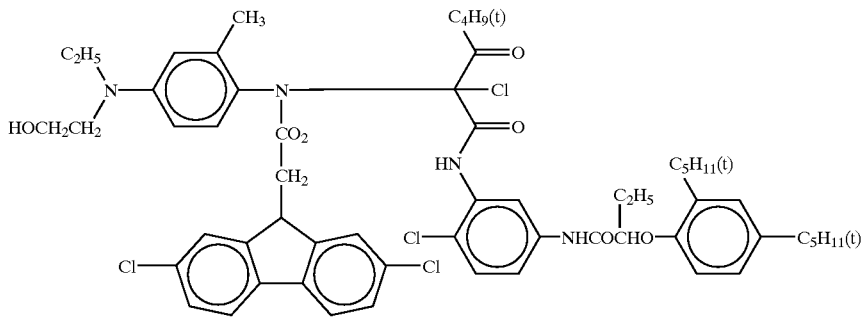

3.
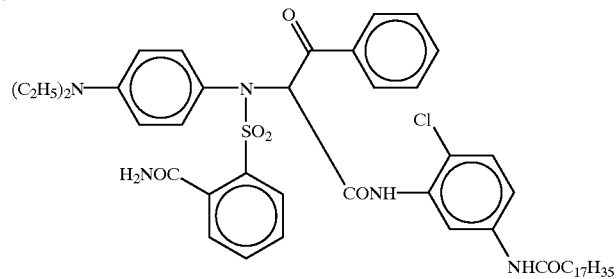
4.
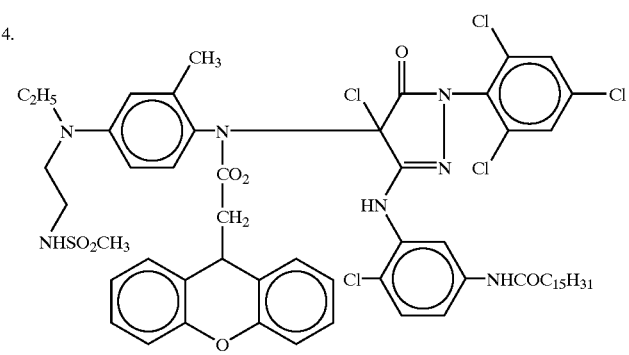
5.
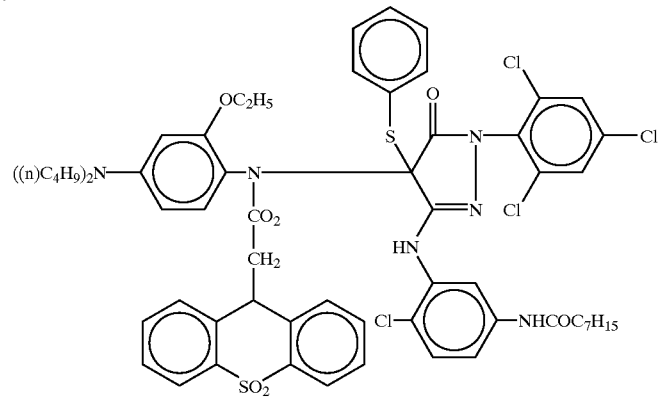
6.
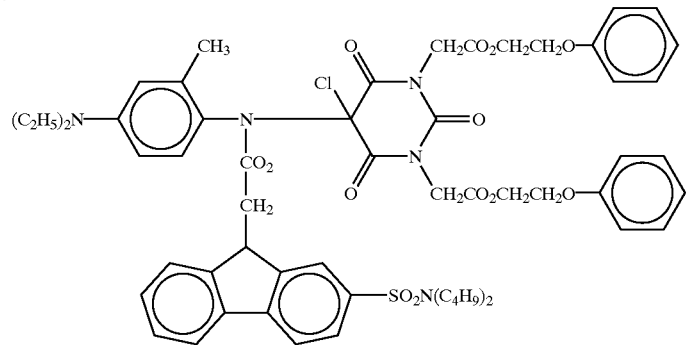

7.
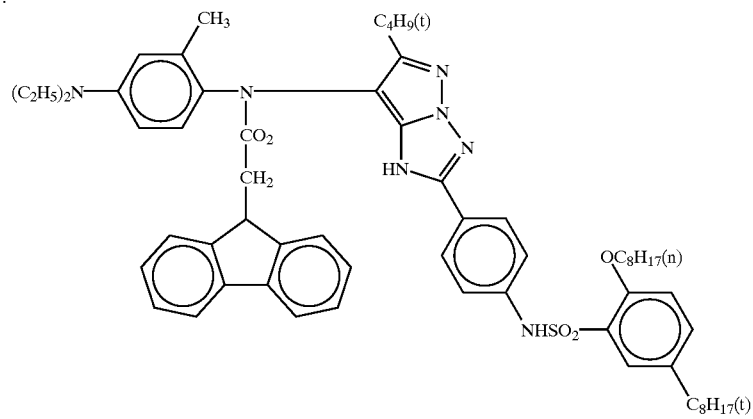
8.
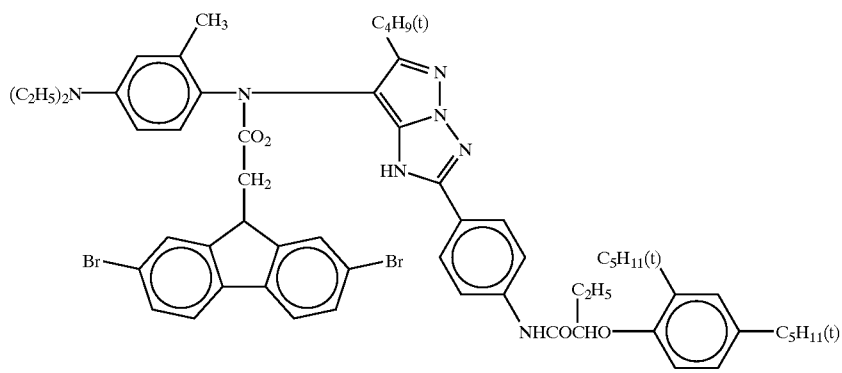
9.
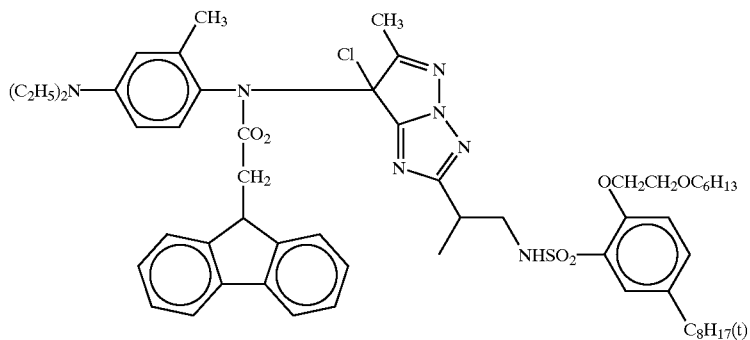
10.
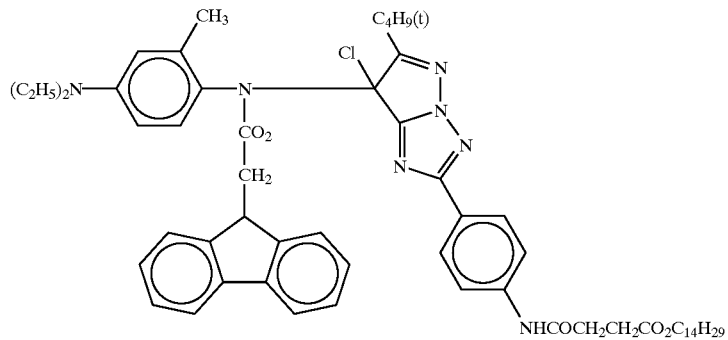

11. 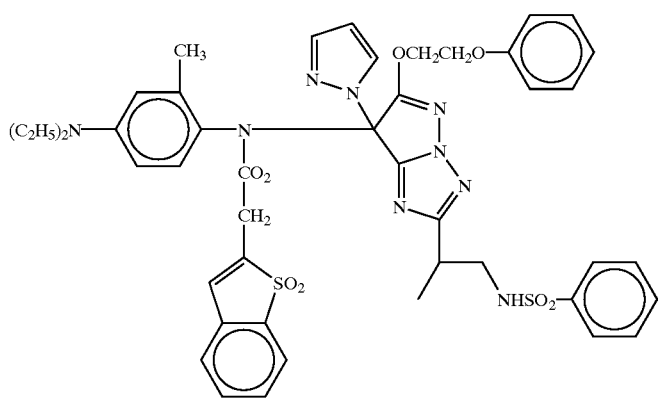
12. 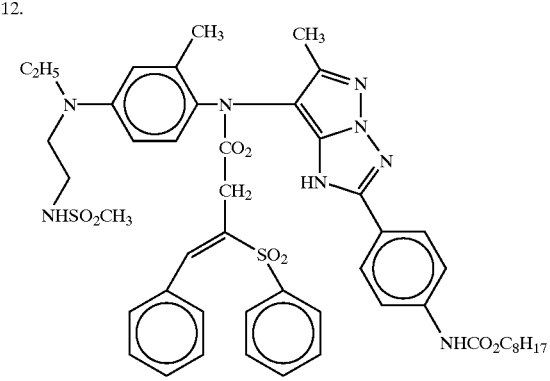
13. 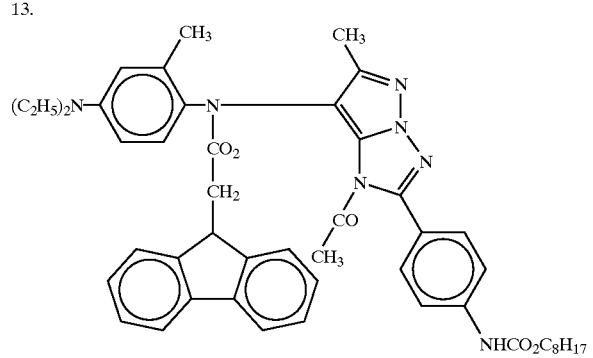
14. 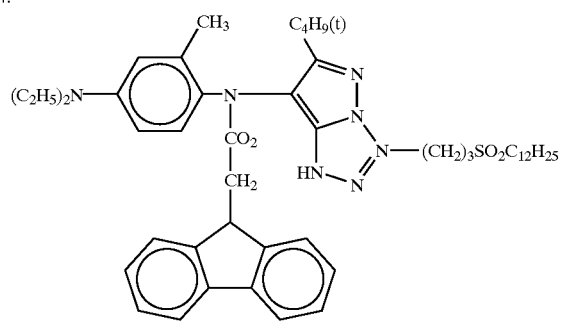

15. 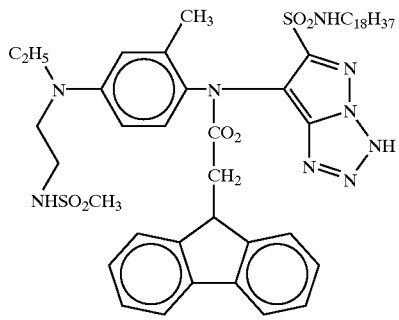
16. 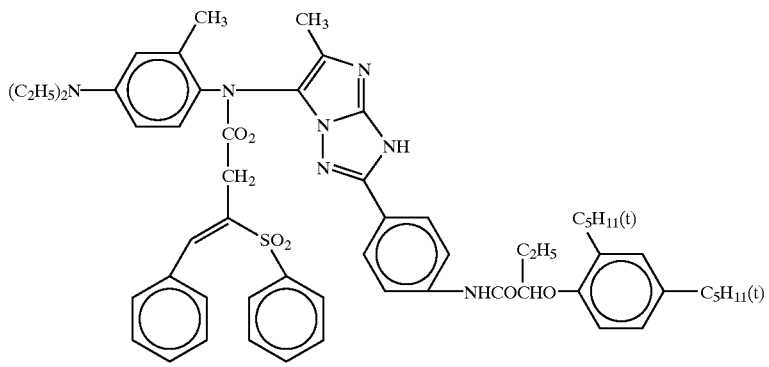
17. 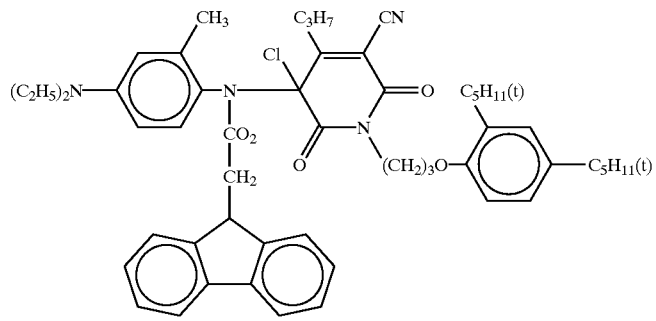
18. 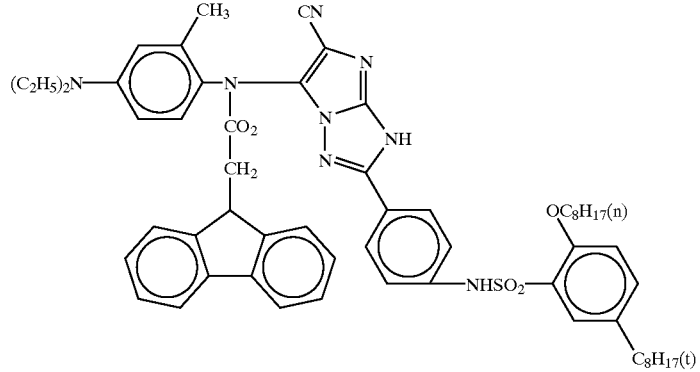

-continued
19.
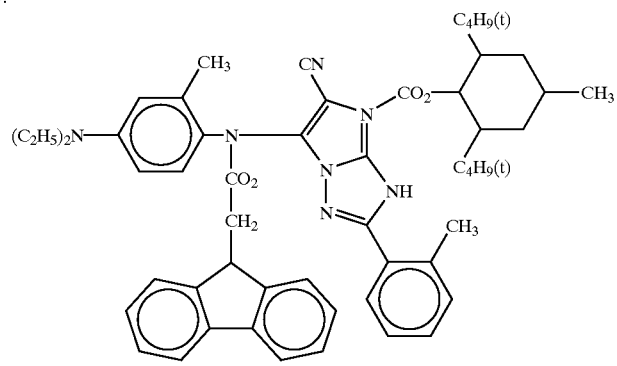
20.
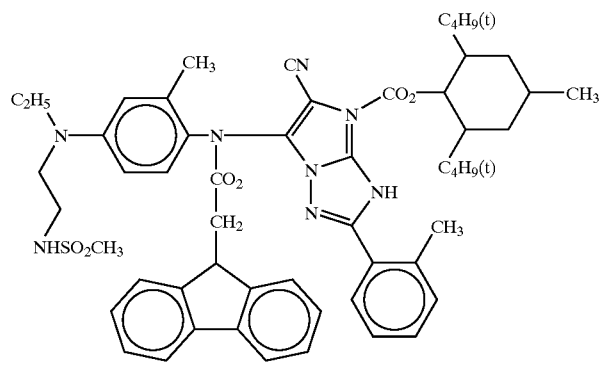
21.
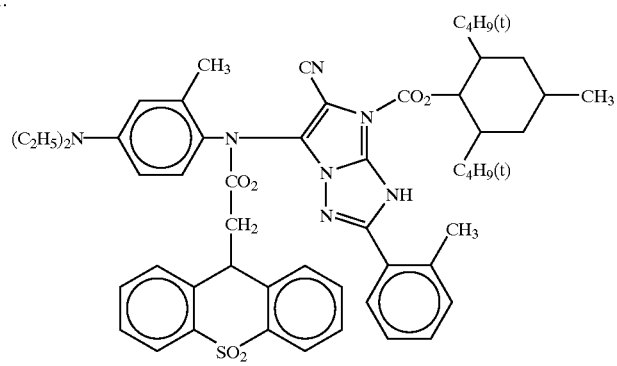
22.
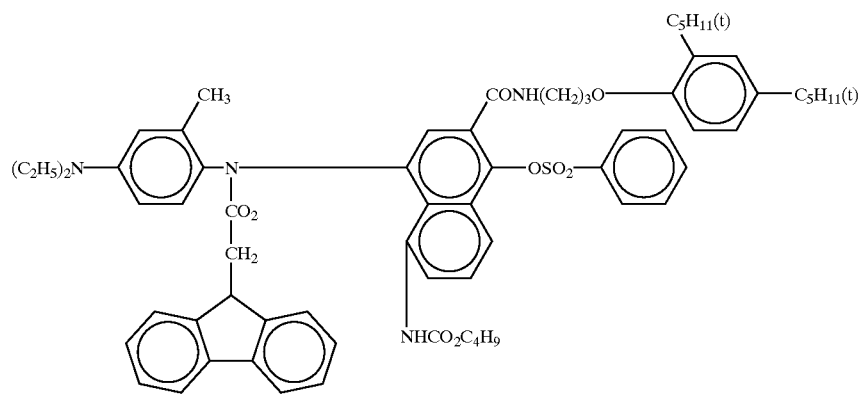

23.
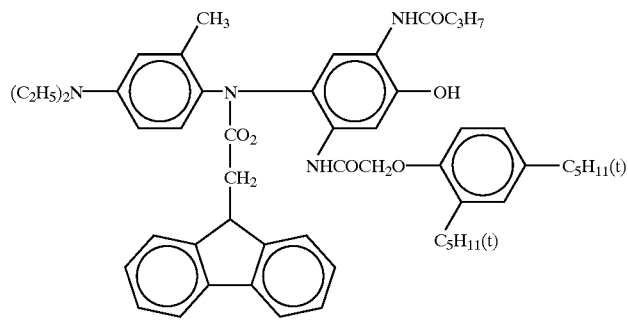
24.
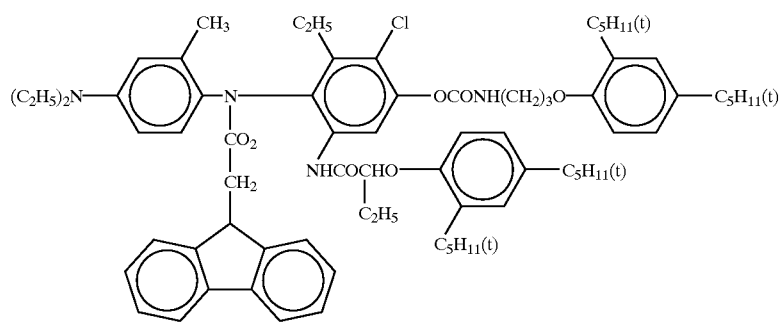
25.
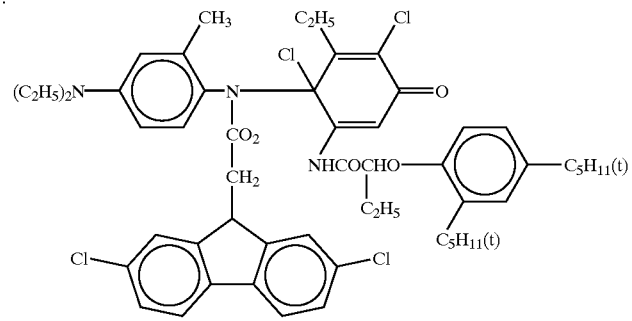
26.
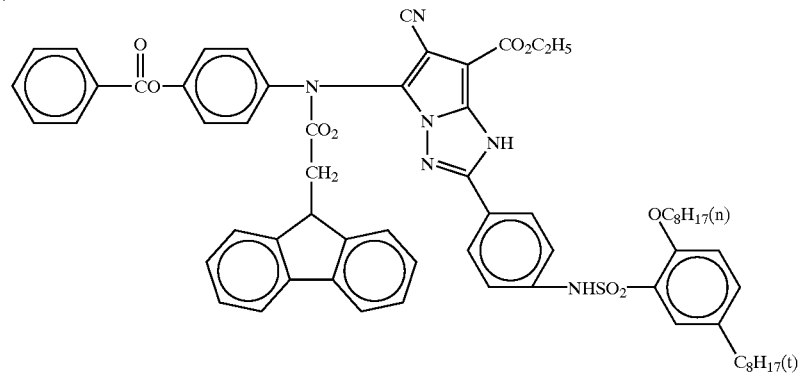

27.

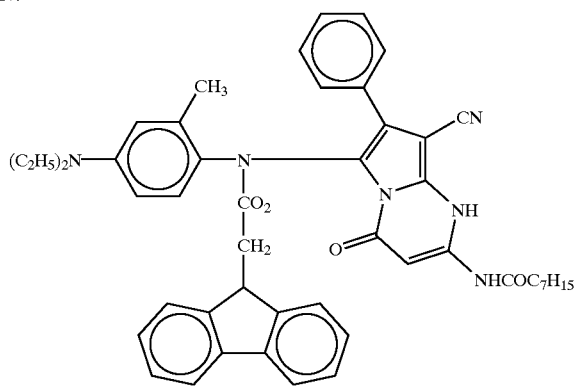

28.

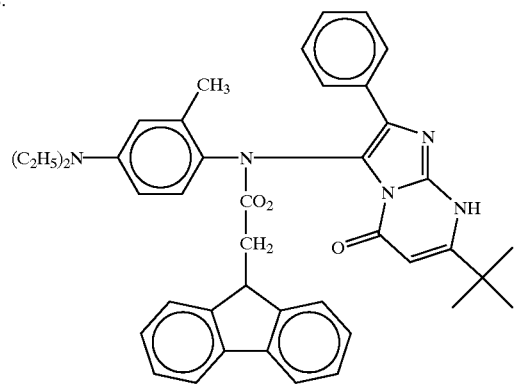

The dye precursor according to the first embodiment of the present invention can be synthesized through an oxidation coupling reaction of a developing agent having a protective group which can be eliminated by a base and a 4-equivalent coupler or 2-equivalent coupler. Further, it can also be synthesized by using a method in which a dye is generated through a reaction of a developing agent and a coupler, the obtained dye is reduced so as to make a leuco dye, and the leuco dye is then made to react with a protective group which can be eliminated by a base.

Methods for synthesizing the dye precursor A represented by the aforementioned formula (1) and the dye precursor B represented by the aforementioned formula (2) are indicated hereinafter.

(Method 1—method for Synthesizing the Dye Precursor A)

Water (100 ml) and acetonitrile (300 ml) were added to 2-amino-5-(diethylamino) toluene-basic acid (42.9 g) (0.2 mol) and the result was dissolved. To the resultant solution was added sodium hydrogencarbonate (37 g)(0.44 mol). The obtained mixture was cooled to 10° C. 9-fluorenylmethylchlorohomate (50 g)(0.193 mol) was added to the cooled mixture over 10 minutes.

After the resultant mixture was stirred for 2 hours at room temperature, water was added to the mixture, and a solid was precipitated therefrom, filtered, and rinsed with water. As a result, 2-(9-fluorenylmethyloxycarbonyl) amino-5-(diethylamino) toluene was obtained as a white solid (75.6 g, yield: 98%). The obtained white solid had physical properties described below.

[m.p.: 141° C., $^1$H-NMR (CDCL$_3$): δ 7.75 (d, 2H), 7.64 (brs, 1H), 7.20–7.45 (m, 6H), 6.52 (d, 2H), 6.19 (brs, 1H), 4.50 (brs, 2H), 3.33 (q, 4H), 2.20 (s, 3H), 1.12 (t, 6H)]

Next, a reaction formula in this method is shown below.

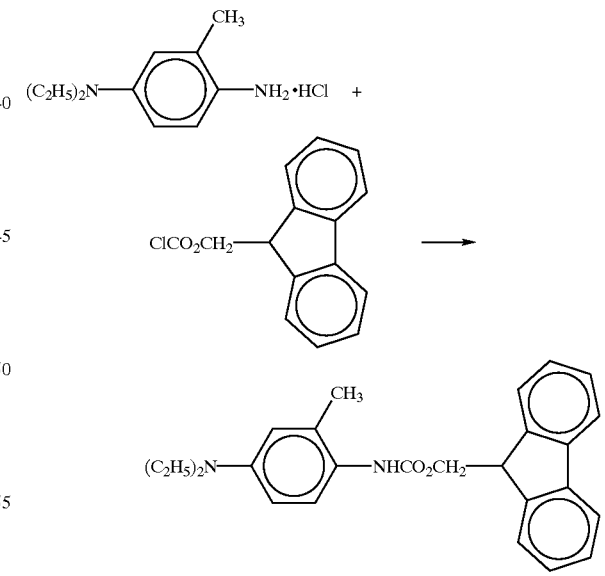

Ethyl acetate (800 ml) was added to 2-(9-fluolenylmethyloxycarbonyl) amino-5-(diethylamino) toluene (16 g)(40 mmol), and 2-[4-(2-n-octyloxy-5-t-octyl) phenylsulfonylamino]phenyl-6-t-butyl-1H-pyrazolo[1,5-b][1,2,4]triazole (25. 4 g)(40 mmol) and the result was dissolved. To the resultant solution was added a 10% aqueous solution of sodium carbonate (400 ml) while stirring, and potassium hexacyanoferrate (III)(27.6 g)(83.8 mol) was then added. The obtained mixture was stirred for two hours at room temperature.

After the reaction, the obtained solution was separated, and the organic layer was dried, and condensed. Acetonitrile was added to the obtained residue and a precipitated solid was filtered. The resultant solid was recrystalized with ethyl acetate/n-hexane, and 2-[4-(2-n-octyloxy-5-t-octyl) phenyl sulfonylamino]phenyl-6-t-butyl-7-[N-(9-fluorenylmethyloxycarbonyl)-N-(2-methyl-4-diethylaminophenyl)]amino-1H-pyrazolo[1,5-b][1,2,4] triazole (the compound in the aforementioned specific example 7) was obtained as a white solid (24 g, yield: 58%). The obtained white solid had physical properties as described below:

[m.p.: 185° C., $^1$H-NMR (CDCL$_3$): δ 7.82 (d, 1H), 7.65 (brs, 2H), 7.57 (brs, 2H), 7.45 (dd, 1H), 6.80–7.25 (m, 11H), 6.40 (brs, 1H), 6.30 (brs, 1H), 4.50 (brs, 2H), 4.16 (t, 2H), 3.23 (q, 4H), 2.20 (brs, 3H), 1.90–2.00 (m, 2H), 1.25–1.60 (m, 18H), 1.00–1.13 (m, 15H), 0.90 (t, 3H), 0.52 (s, 9H)]

A reaction formula in this method is shown hereinafter:

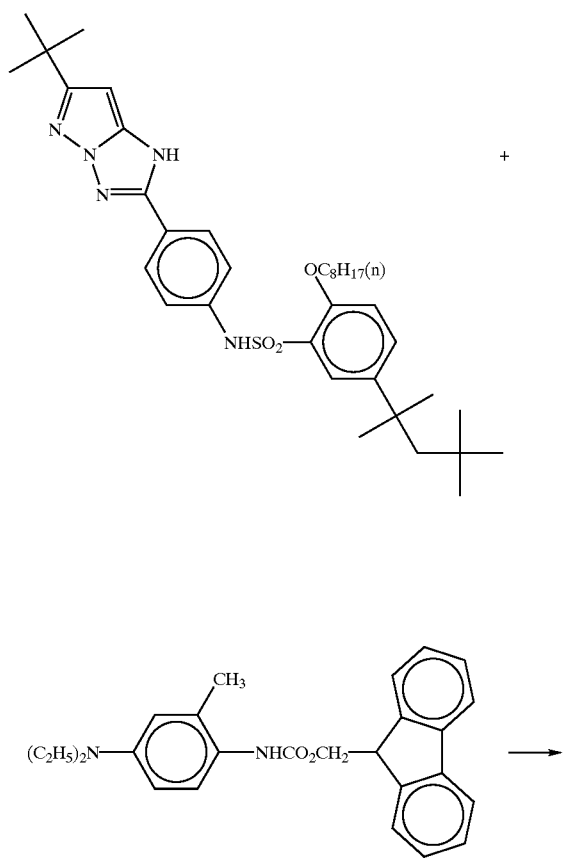

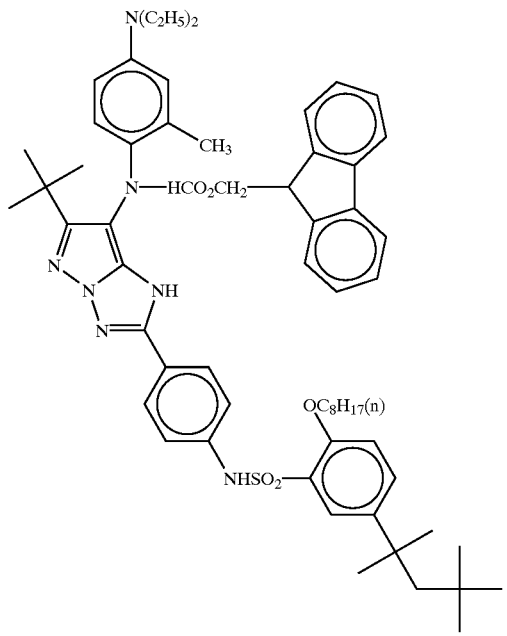

An ethylacetate solution of the aforementioned white solid (5×10$^{-5}$ mol) was prepared. When pentylamine (2 ml) was added to the obtained solution (2 ml) at room temperature, the obtained solution speedily formed a magenta color.

(Method 2—Method for Synthesizing the Dye Precursor B)

Ethyl acetate (200 ml) was added to 2-(9-fluorenylmethyloxycarbonyl) amino-5-(diethylamino) toluene (4 g)(10 mmol), and 2-[4-(2-n-tetradecyloxycarbonyl) ethylcarbonylamino]phenyl-6-t-butyl-7-chloro-1H-pyrazolo [1,5-b][1, 2, 4]triazole (5.86 g)(10 mmol). The obtained mixture was heated to a temperature of 50° C., and dissolved. The obtained solution was cooled to room temperature. To the solution was added a 10% aqueous solution of sodium carbonate (100 ml), while stirring. Then, potassium hexacyanoferrate (III) (6.91 g) (21 mmol) was added to the obtained solution. The resultant mixture was stirred for four hours at room temperature. After reaction, the mixture was separated, and its organic layer was dried, and condensed. The resultant residue was purified by silica gel chromatography (ethyl acetate/n-hexane=2/3), and recrystalized with ethyl acetate/acetonitrile. 2-[4-(2-n-tetradecyloxycarbonyl) ethylcarbonylamino]phenyl-6-t-butyl-7-[N-(9-fluorenylmethyloxycarbonyl)-N-(2-methyl-4-diethylaminophenyl)]amino-7-chloro-7H-pyrazolo[1,5-b] [1,2,4]triazole (the compound in the specific example 10) was obtained as a white solid (5 g, yield: 51%). The obtained white solid had physical properties as described below:

[m.p.: 160° C., $^1$H-NMR (COCL$_3$): δ 8.16 (brs, 1H), 7.80 (brs, 2H), 7.52–7.67 (m, 4H), 7.03–7.20 (m, 4H), 6.85–6.95 (m, 3H), 6.44 (brs, 1H), 6.35 (brs, 1H), 4.60 (brs, 2H), 4.09

(t, 2H), 3.21 (q, 4H), 2.70 (t, 2H), 2.65 (t, 2H), 2.25 (brs, 3H), 1.57–1.70 (m, 2H), 1.25 (s, 22H), 0.93–1.15 (m, 15H), 0.90 (t, 3H)]

A reaction formula in this method is shown as follows:

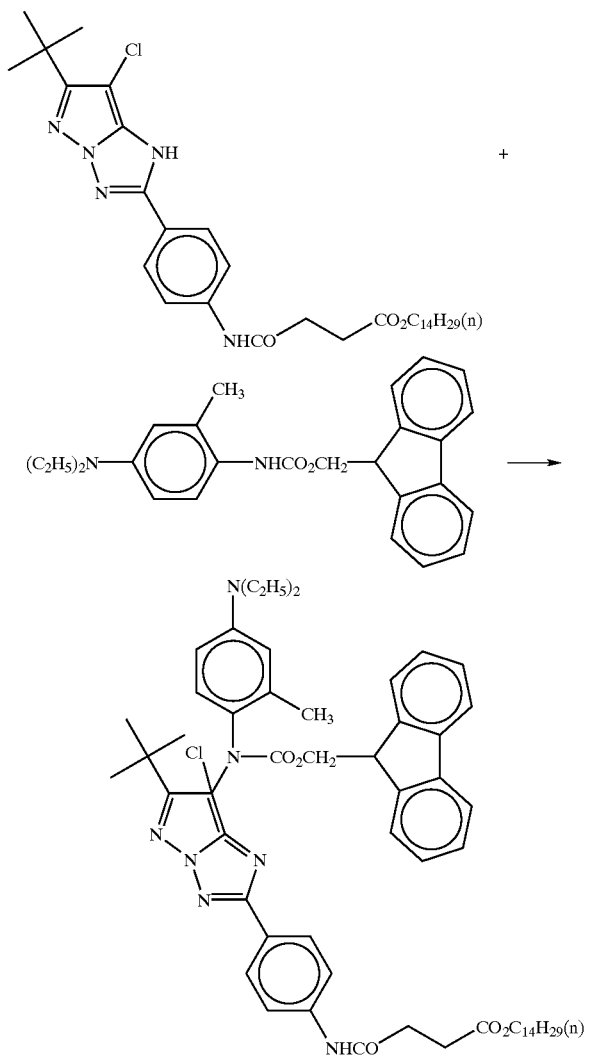

An ethyl acetate solution of the aforementioned white solid ($5 \times 10^{-5}$ mol) was prepared. When DBU (1,8-diazabicyclo[5,4,0]-7-undethene) (2 ml) was added to the obtained solution (2 ml) at room temperature, the solution rapidly formed a magenta color.

(Method 3—Method for Synthesizing the Dye Precursor A)

The following compound [1] (21.5 g), water (50 ml), and ethyl acetate (150 ml) were independently measured, and charged into a three-necked flask, stirred, and the result was dissolved. To the obtained solution was gradually added sodium hydrogencarbonate (14.7 g) at room temperature. Thereafter, the resultant mixture was cooled to a temperature of 5° C. by using an ice-water bath. To the obtained solution was gradually added the following compound [2] (12.9 g) over five minutes, and the result was stirred for two hours at room temperature. To the reaction solution were added water (100 ml) and ethyl acetate (100 ml) so as to extract a product. The obtained product was washed with water, and an ethyl acetate layer was dried by magnesium sulfate. Thereafter, the solvent was evaporated and removed, thus obtaining a white solid. In addition, after dissolving the white solid in $CH_3OH$, the white solid was recrystallized, thus obtaining the following compound [3] (17.3 g, yield: 70%).

A reaction formula is shown below:

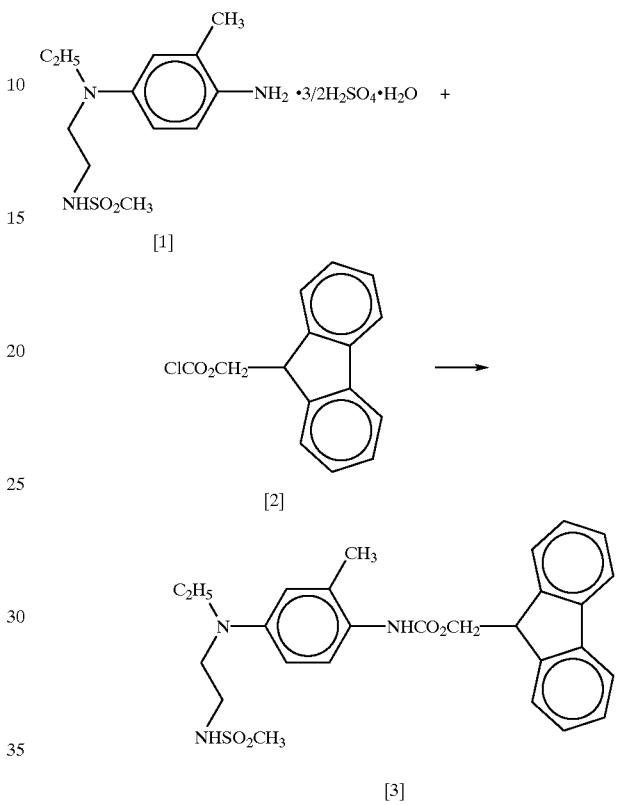

Physical properties of the obtained aforementioned compound [3] are represented as follows:

[$^1$H-NMR (DMSOd6): δ 8.70 (brs, 2H), 7.91 (d, 2H), 7.65 (brs, 1H), 7.30–7.48 (m, 4H), 7.16 (t, 1H), 6.93 (brs, 1H), 6.53 (s, 1H), 6.47 (d, 1H), 4.73 (brs, 2H), 4.28 (brs, 1H), 3.33 (q, 2H), 3.07 (q, 2H), 2.90 (s, 3H), 2.10 (s, 3H), 1.06 (t, 3H)]

The obtained aforementioned compound [3] (12.3 g) and the following compound [4] (10.7 g) were measured respectively and charged into a three-necked flask, and ethyl acetate (200 ml) was added to these compounds. The temperature of the resultant solution was set at 55° C., and activated manganese dioxide (10.9 g) was added gradually thereto. The result was stirred for eight hours at the temperature of 60° C. The reaction solution was filtrated by using Celite, and the resultant solid was washed with water, and dried by magnesium sulfate. Thereafter, a solvent was evaporated and removed. A residue was purified by silica gel column chromatography (an eluting solvent: ethyl acetate/n-hexane=1/1), thus obtaining the compound in the aforementioned specific example 20 as a dried-up substance (13 g, yield: 60%). As a result of mass spectrometry, the value was found to correspond to that of the desired result. A reaction formula is represented as follows:

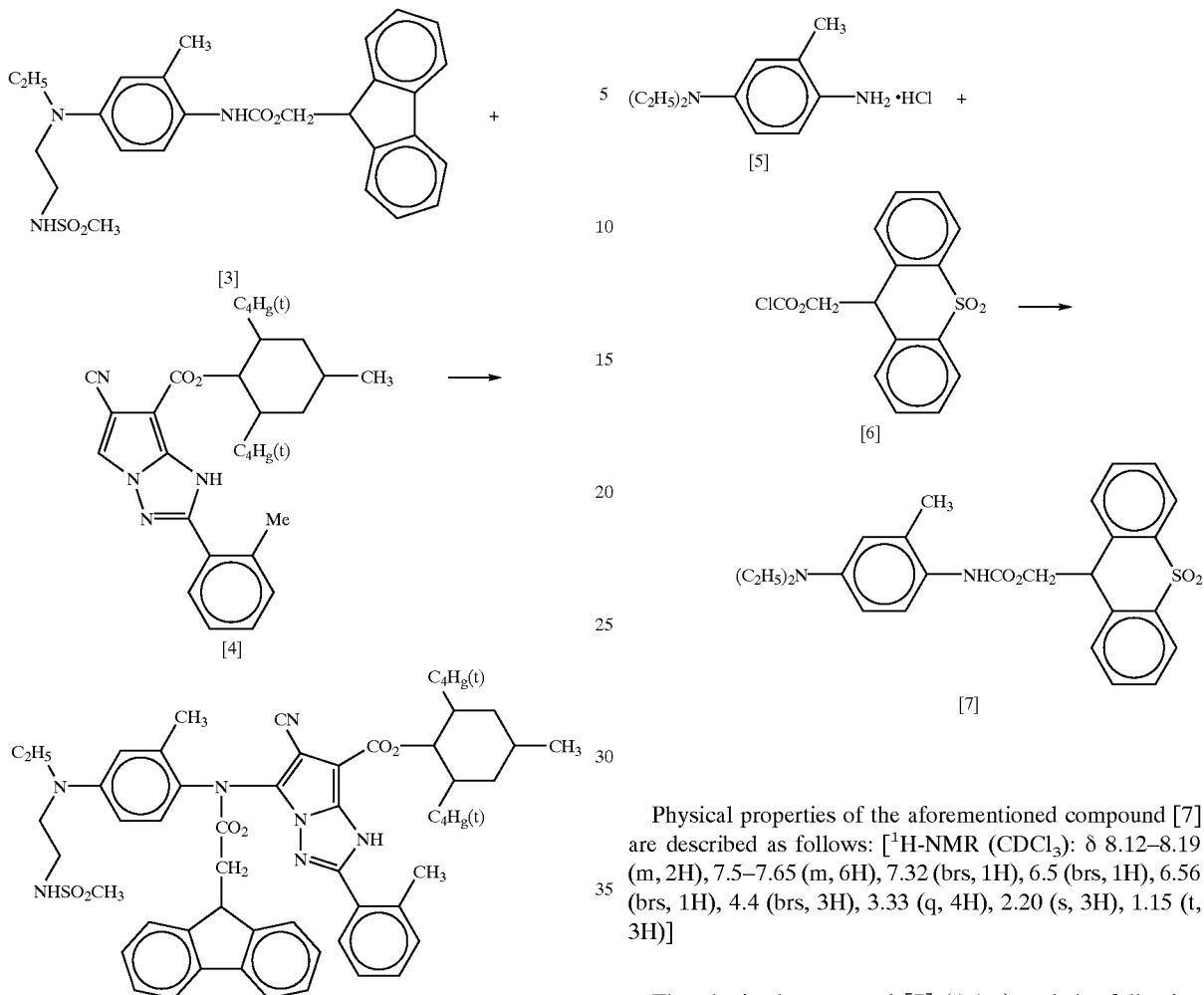

A methanol solution of the obtained compound (5×10⁻⁵ mol) in the specific example 20 was prepared. When morpholine (2 ml) was added to the resultant solution (2 ml) at room temperature, the obtained solution formed a cyan color.

(Method 4—Method for Synthesizing the Dye Precursor A)

The following compound [5] (10.7 g), water (30 ml), and acetonitrile (100 ml) were measured and charged into a three-necked flask, stirred, and the result was dissolved. To this obtained solution was added gradually sodium carbonate (12.6 g) at room temperature. Thereafter, the obtained mixture was cooled to 5° C. by using an ice-water bath. To the obtained solution was added the following compound [6] (16.1 g) over ten minutes, and the result was stirred for two hours at room temperature. To the reaction solution was added water (500 ml) so as to precipitate a white solid. The precipitated white solid was filtrated and washed with water so that the following compound [7] was obtained (19.0 g, yield: 82%).

A reaction formula of this compound is represented as follows:

Physical properties of the aforementioned compound [7] are described as follows: [$^1$H-NMR (CDCl$_3$): δ 8.12–8.19 (m, 2H), 7.5–7.65 (m, 6H), 7.32 (brs, 1H), 6.5 (brs, 1H), 6.56 (brs, 1H), 4.4 (brs, 3H), 3.33 (q, 4H), 2.20 (s, 3H), 1.15 (t, 3H)]

The obtained compound [7] (4.6 g) and the following compound [4] (4.7 g) were measured and charged into a three-necked flask, and chloroform (40 ml) was added thereto. The temperature of the obtained solution was set to 50° C. To the solution was added gradually manganese dioxide (4.4 g), and the result was stirred for 6 hours. The reaction solution was filtrated by using Celite, the resultant solid was washed with water, and the solvent was evaporated and removed. A residue was purified by silica gel column chromatography (eluted solution: ethyl acetate/n-hexane=1/1), to thereby obtain the compound in the aforementioned specific example 21 as a dried-up substance (4.1 g, yield: 44%). As a result of mass spectrometry, the value was found to correspond to that of the desired result. A reaction formula of the compound will be shown as below:

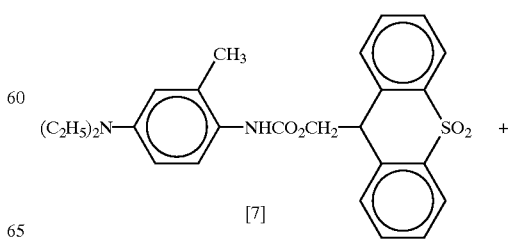

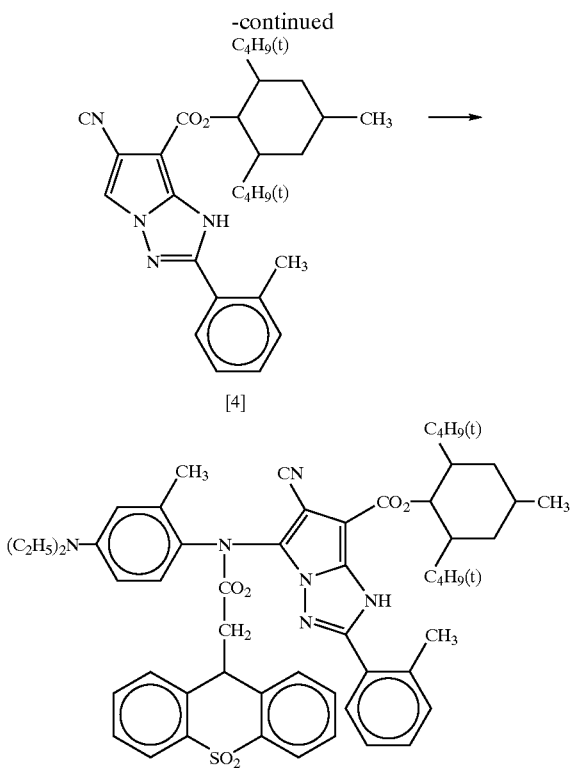

[4]

A methanol solution of the obtained compound ($5 \times 10^{-5}$ mol) in the specific example 21 was prepared. When triethylamine (2 ml) was added to the obtained solution (2 ml) at room temperature, the solution formed a cyan color.

The dye precursor according to the first embodiment of the present invention forms color promptly through contact with a base, at room temperature, or within a range of temperature at which it is impossible for the dye precursor to form color without a base even if the dye precursor is heated. In order to increase the speed of this color-forming reaction, an oxidant can be used together with the dye precursor. Examples of the oxidant include: quinones such as 2,3-dichloro-5,6-dicyano-1,4-benzoquinone, and tetrachloro-1,4-benzoquinone; nitro compounds such as nitrobenzene and m-nitrobenzenesulfonic acid, nitroso compounds such as nitrosobenzene, cations such as triphenylcation, azo compounds such as diethyl azodicarboxylate, nitroxides such as diphenylnitroxide, porphyrexide, and 2,2,6,6-tetramethylpiperidine-1-oxyl, and N-oxides such as pyridine-N-oxides.

Since the dye precursor according to the first embodiment of the present invention has the characteristic of forming color promptly upon contact with a base as described above, when it is used as a color-forming compound of the image forming material having an image forming layer on a support, the obtained image forming material can exhibit excellent color-formation with a small amount of energy, and images on the image forming material are excellent in terms of storage stability.

Second Embodiment of the Present Invention

An image forming material and an image forming method using the same according to a second embodiment of the present invention will be explained hereinafter.

The second embodiment of the present invention is an image forming material and an image forming method using the same, wherein the image forming material has an image forming layer on a support, the image forming layer containing at least one type of each of a photopolymerization initiator, a dye precursor which can form color through contact with a base, a base or a base precursor, and a polymerizable compound.

[Image Forming Material]

A more detailed description of each of elements structuring the image forming material according to the second embodiment of the present invention will be given hereinafter.

A: Support

As the support used for the image forming material of the present invention, a paper support used for conventional pressure-sensitive paper and heat-sensitive paper, or for dry or wet diazo-copy paper can be used. Specific examples of the support include: acid paper, neutralized paper, coated paper, plastic film laminated paper in which plastic such as polyethylene is laminated to paper, synthetic paper, and plastic film such as polyethylene telephthalate or polyethylene naphthalate. In order to correct a curl balance of a support, or in order to prevent chemicals or the like from penetrating into a back side of the support, a back coat layer can be provided. This back coat layer can be provided in the same manner as a protective layer, which will be described later. Further, a stripping paper can be combined therewith at a back side of the support via an adhesive layer, to form a label. Moreover, the support can be used as a stripping paper by disposing an adhesive layer on the image forming layer so as to form a so-called seal. The support can contain fluorescent brighteners, blueing dyes, pigments, and the like.

Further, in a case in which a transparent material is used as the support, image writing in an optical image forming process which will be described later, or light irradiation in a developing process can be carried out from a support surface side of the image forming material.

B: Image forming layer

A description of various materials for structuring the image forming layer, and a specific structure of the image forming layer will be given hereinafter.

(Photopolymerization Initiator)

As the photopolymerization initiator, known photopolymerization initiators such as benzophenol derivatives and acetophenone derivatives can be used. Specific examples thereof include: α-hydroxy- or α-aminoacetophenone, 4-aroyl-1,3-dioxolane, benzoyl alkyl ether and benzyl ketal, monoacyl phosphine oxide, bis acyl phosphine oxide or titanocene, ferrocene, anthraquinone, thioxanthone or xanthone, and the like. Further examples include the following combinations: a dye and iodonium salt; a dye and benzoin ether; a dye and s-triazines having a trihalogen substituted methyl group; a dye and an organic peroxide; a dye and azinium salt; and a dye and an organic boron compound.

Among these combinations in terms of photosensitive wavelengths and radical formation efficiency, a combination of a dye and an organic boron compound is preferable, and a combination of a dye and an organic boron compound represented by the following formula (3) is more preferable as the photopolymerization initiator.

Formula (3):

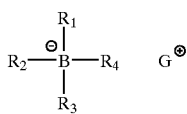

wherein $R_1$ to $R_4$ independently represent an alkyl group, an aryl group, a heterocyclic group, or $SiR_5R_6R_7$; $R_5$, $R_6$ and $R_7$ independently represent an alkyl group and an aryl group; and $G^+$ represents a group which is able to form a positive ion.

In the aforementioned formula (3), preferably, at least one of $R_1$ to $R_4$ is an alkyl group.

Further, using in combination, a plurality of types of photopolymerization initiators formed by an organic boron compound and a dye and/or other types of photopolymerization initiators is also preferable in order to change photosensitive wavelengths thereof.

A detailed description of the organic boron compound represented by the aforementioned formula (3) will be given hereinafter.

In the aforementioned formula (3), as the alkyl group represented by $R_1$ to $R_4$, an alkyl group having 1 to 18 carbon atoms is preferably used, and an alkyl group having 1 to 12 carbon atoms is more preferably used. The alkyl group can have an unsaturated bond and may be a straight or branched chain.

In the aforementioned formula (3), as the aryl group represented by $R_1$ to $R_4$, an aryl group having 6 to 26 carbon atoms is preferably used, and a phenyl group or a naphthyl group is more preferably used.

The alkyl group and the aryl group can be further substituted by an alkyl group, an aryl group, an alkoxy group, an aryloxy group, an alkyl thio group, a halogen atom, an alkoxycarbonyl group, an aryloxycarbonyl group, an acyloxy group, CN, and $NO_2$.

In the aforementioned formula (3), as an example of a heterocyclic group, those having furan, thiophene, pyrrole, imidazole, pyrazole, triazole, pyridine, and pyrimidine rings can be listed.

In the aforementioned formula (3), examples of $SiR_5R_6R_7$ include trimethylsilyl, triphenylsilyl, dimethylphenylsilyl, di-t-butylphenylsilyl, and the like.

In the aforementioned formula (3), as described above, $G^+$ is a group which is able to form a positive ion. Examples of these groups include an alkaline metal (especially, lithium or sodium), an alkaline metal, a transition metal, a quaternary ammonium, and a dye cation or cationic transition metal coordination complex compound. Ammonium, tetraalkyl ammonium, or a dye cation is preferable. Tetraalkyl ammonium is represented by the following formula:

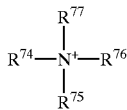

Each ofr $R^{74}$ to $R^{77}$ independently represents an alkyl group. Examples of the tetraalkyl ammonium include: tetramethyl ammonium in which each of $R^{74}$ to $R^{77}$ represents a methyl group; tetraethyl ammonium in which each of $R^{74}$ to $R^{77}$ represents an ethyl group; tetrapropyl ammonium in which each of $R^{74}$ to $R^{77}$ represents a propyl group; and tetrabutyl ammonium in which each of $R^{74}$ to $R^{77}$ represents a butyl group.

As $G^+$, benzyl trialkyl ammonium represented by the following formula is preferable.

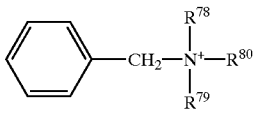

wherein each of $R^{78}$ to $R^{80}$ independently represents an alkyl group. Preferable examples of benzyl trialkyl ammonium include benzyl trimethyl ammonium, benzyl triethyl ammonium, benzyl tripropyl ammonium, and benzyl tributyl ammonium. Further, trisalkyl ammonium such as trimethyl ammonium is preferable. Examples of $G^+$ include a phosphonium ion and an ammonium ion, described below:

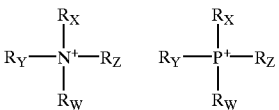

wherein $R_W$, $R_X$, $R_Y$ and $R_Z$ independently represent a hydrogen atom, an unsubstituted or substituted alkyl group, a cycloalkyl group, an alkenyl group, a phenyl group, or an arylalkyl group. Specific examples of substituents of these alkyl, cycloalkyl, alkenyl, phenyl and arylalkyl groups include: a halogen atom; a hydroxyl group; a heterocycloalkyl group (such as an epoxy group, an aziridyl group, an oxetanyl group, a furanyl group, a pyrrolidinyl group, a pyrrolyl group, a thiophenyl group, or a tetrahydrofuranyl group); a dialkylamino group; an amino group; a carboxyl group; alkyl or aryl carbonyl group, and an aryloxy or alkoxycarbonyl group. A tetravalent nitrogen atom can be a part of 5 or 6-member ring, or a condensed ring. This ring can further contain another hetero atom such as S, N, or O.

Moreover, $G^+$ can be a polyammonium ion or a polyphosphonium ion in which the aforementioned ammonium ions are bonded to each other or phosphonium ions are bonded to each other, respectively, and a bisammonium or bisphotophonium ion is particularly preferable. As an example of a substituent in a case in which the poly-ion is substituted, a substituent which is the same as that of the aforementioned mono-ion can be listed.

The aforementioned ammonium ion and phosphonium ion can be substituted by a neutralized dye (e.g., thioxanthene, thioxanthone, coumarin, ketocoumarin or the like). Such ions can be obtained through a reaction of an ammonium ion or a phosphonium ion which is substituted by reaction groups (e.g., an epoxy group, an amino group, a hydroxyl group, and the like), together with an appropriate neutralized dye. A method for synthesizing such ions is, for example, disclosed in EP-A No. 224967 (Quantacure QTX).

An ammonium ion and a phosphonium ion can be also substituted by an electron receptive colorless compound (e.g., benzophenone). Examples of $G^+$ in a case in which the ammonium ion is substituted by benzophenone are described below. However, the present invention is not limited to these examples.

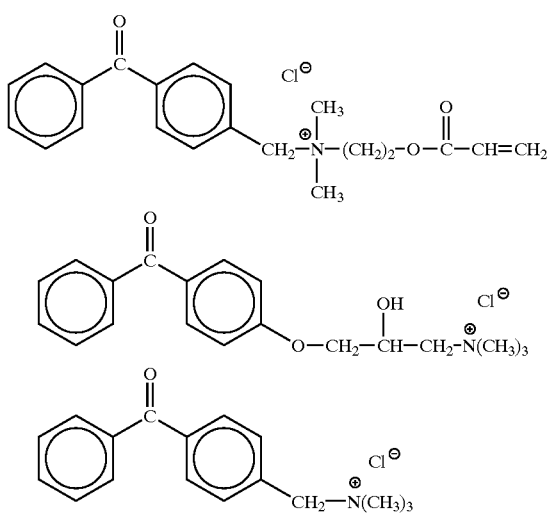

Examples of other quaternary ammonium include trimethyl cetyl ammonium ion and cetyl piridinium ammonium ion.

As other examples of G⁺, cations in cation group No. 1 shown below can be listed:

Cation Group No. 1:

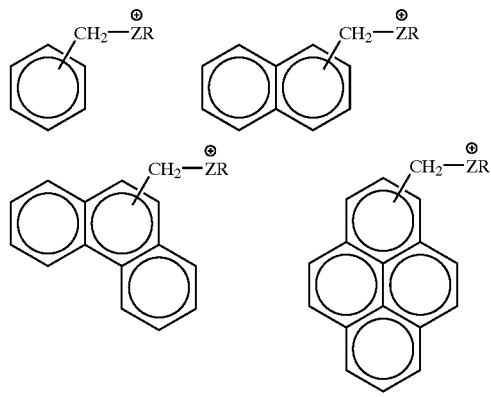

wherein Z represents P, S or N; and R represents an alkyl group or an aryl group.

As other examples of G⁺, cations from cation group No. 2 or cation group No. 3 described below can be listed. In the formula of the cation group No. 2 described below, R represents an alkyl group or an aryl group. These cations are described in J. Polymer Science Part A: Polymer Chem. 1992, 30, 1987, and in Polymer 1993, 34 (6), 1130, researched by both by Yaguchi et al. In the formula of the cation group No. 3, R' represents an unsubstituted or substituted benzyl group or a phenacyl group. These cations are disclosed in JP-A No. 7-770221. An aromatic ring in a pyrimidinium site of these cations can be substituted.

Cation Group No. 2:

Cation Group No. 3:

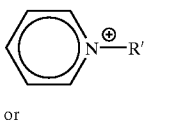

or

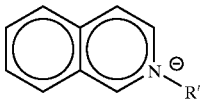

Other examples of the positive ion G⁺ include other onium ions such as an jodonium ion or a sulfonium ion. Examples of this cation are disclosed in EP-A Nos. 555058 and 690074. Cations represented by the following formula can be also used.

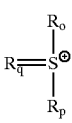

Further, as G⁺, cations described below are preferable.

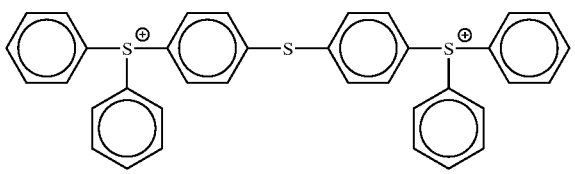

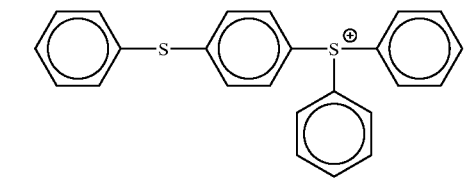

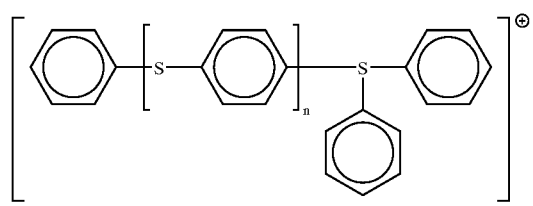

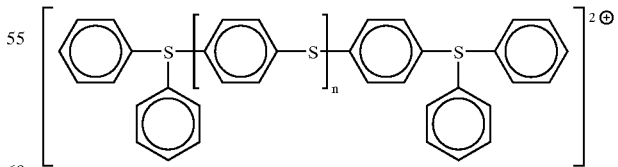

As other examples of G⁺, cations described below can be listed. In the following formula, $R_g$ represents an alkyl group, particularly an ethyl group or a benzyl group. Moreover, the aromatic ring can have substituents.

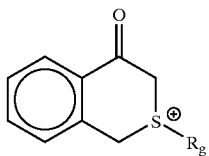

G+ can be a halonium ion. Diaryliodonium ions disclosed in EP-A Nos. 334056 and 562897 are particularly preferable.

Further, for example, a ferrocenium cation which is represented by the following formula and which is disclosed in EP-A Nos. 94915 and 109851 is preferable:

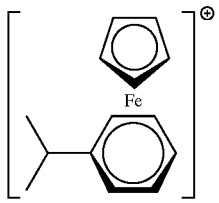

G+ can be an onium ion such as an ammonium ion, a phosphonium ion, a sulfonium ion, an iodonium ion, a cellonium ion, an arsonium ion, a terronium ion, and a bismsonium ion, disclosd in JP-A No. 6-266102.

Further, G+ can be a cationic transition metal complex compound. In this case, compounds as disclosed in U.S. Pat. No. 4,954,414 can be listed. Particularly preferable examples of these compounds include bis(2,2'-bipyridine) (4,4'-dimethyl-2,2'-bipyridine)ruthenium, tris(4,4'-dimethyl-2,2'-bipyridine)ruthenium, tris(4,4'-dimethyl-2,2'-bipyridine)iron, tris(2,2',2"-terpyridine) ruthenium, tris(2,2'-bipyridine)ruthenium, and bis(2,2'-bipyridine)(5-chloro-1, 10-phenanthrine)ruthenium.

G+ can be a cationic dye. As a specific example, a cyanine dye, a cationic dye of triarylmethane, or the like can be used.

The organic boron compound described in the formula (3) can be used in combination with known photopolymerization initiators such as benzophenone; and acetophenone derivatives such as α-hydroxy- or α-aminoacetophenone, 4-aroyl-1,3-dioxolane, benzoyl alkyl ether and benzyl ketal, monoacylphosphine oxide, bisacylphosphine oxide or titanocene, ferrocene, anthraquinone, thioxanthone or xanthone. Examples of especially appropriate photopolymerization initiators include 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4-(2-hydroxyethoxy)-benzoyl]-1-hydroxy-1-methylethane, 1-[4-(acryloyloxyethoxy)-benzoyl]-1-hydroxy-1-methylethane, diphenyl ketone, phenyl-1-hydroxy-cyclohexyl ketone, (4-morphorinobenzoyl)-1-benzyl-1-dimethylaminopropane, 1-(3,4-dimethoxyphenyl)-2-benzyl-2-dimethylamino-buthane-1-on, (4-methylthiobennzoyl)-1-methyl-1-morphorino-ethane, benzyl dimethyl kethal, bis (cyclopentadienyl)-bis(2,6-difluoro-3-pyrrole-1-yl-phenyl) titanium, cyclopentadienyl-arene-ferrite (II) complex salt such as (η6-isopropylbenzene)-(η5-cyclopentadienyl)-iron (II)hexafluorophosphate, trimethylbenzoyldiphenylphosphine oxide, bis(2,6-dimethoxy-benzoyl)-(2,4,4-trimethyl-pentyl)-phophine oxide, bis(2,4,6-trimethylbenzoyl)-2,4-dipentyloxyphenyl-pohsphine oxide or bis(2,4,6-trimethylbenzoyl)phenyl-phosphine oxide.

Another appropriate photopolymerization initiator can be seen in the passage from line 35 of the 20th column, to line 35 of the 21st column in U.S. Pat. No. 4,950,581. Moreover, triazine compounds disclosed in EP-A No. 137452, and DE-A Nos. 2718254 and 2243621 are preferably used. Another appropriate triazine compound can be seen in the passage from line 60 of the 14th column to line 44 of the 18th column in U.S. Pat. No. 4,950,581. An example of a compound which is of interest among trihalomethyltriazines is 2,4-bis(trichloromethyl)-6-(4-styrylphenyl)-s-triazine. In the case in which the organic boron compound described in the formula (3) is used in a hybrid system, cationic photopolymerization initiator in addition to a novel free radical hardening agent is used, for example, peroxide compounds such as benzoyl peroxide (another appropriate peroxide is described from line 17 to 25 of the 19th column in U.S. Pat. No. 4,950,581) and an aromatic sulfonium or iodonium salt which is described for example in the passage from line 60 of the 18th column to line 10 of the 19th column in U.S. Pat. No. 4,950,581 or cyclopentadienyl-arene-iron (II) complex salts such as (η6-isopropylbenzene)-(η5-cyclopentadienyl)-iron (II) hexafluorophosphate.

Specific examples of the organic boron compounds represented by the aforementioned formula (3) are shown below

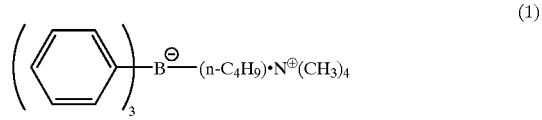

(1)

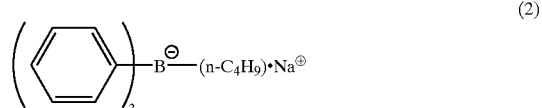

(2)

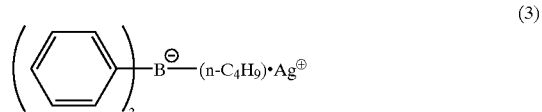

(3)

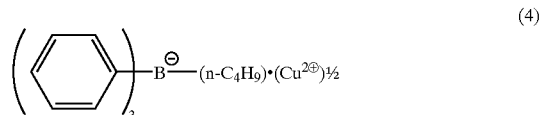

(4)

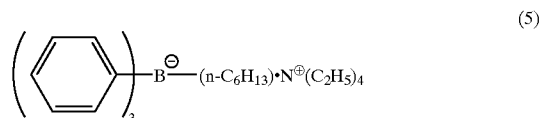

(5)

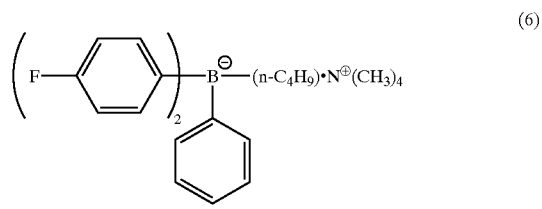

(6)

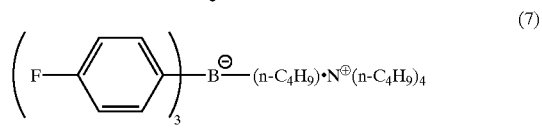

(7)

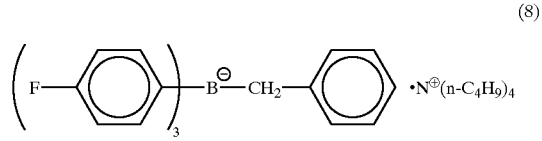

(8)

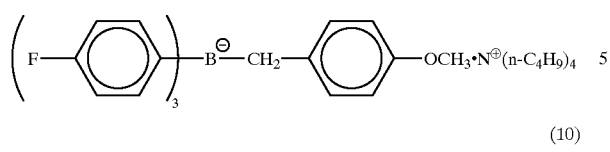
(9)
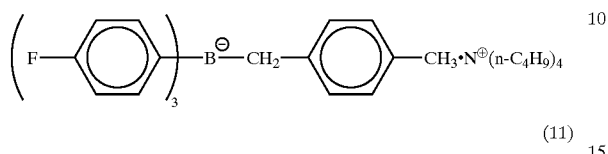
(10)
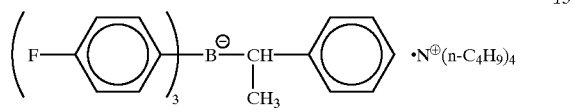
(11)
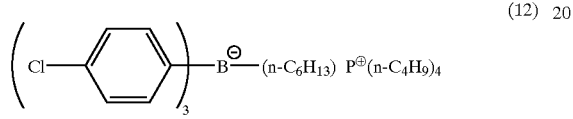
(12)
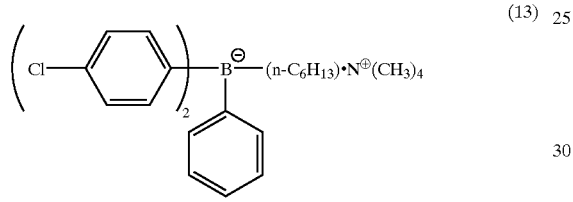
(13)
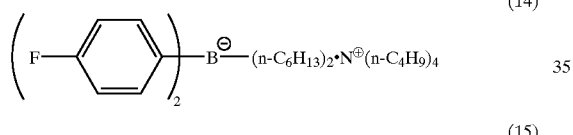
(14)
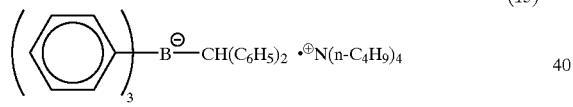
(15)
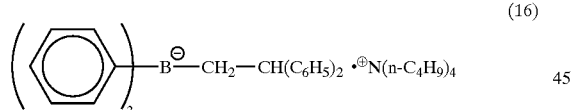
(16)
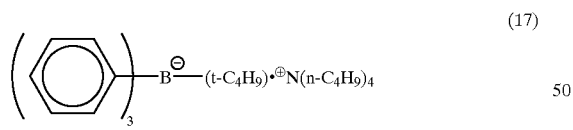
(17)
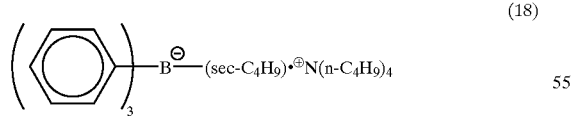
(18)
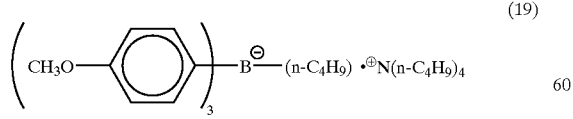
(19)
(20)
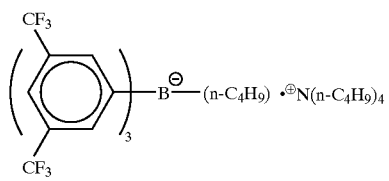
(21)
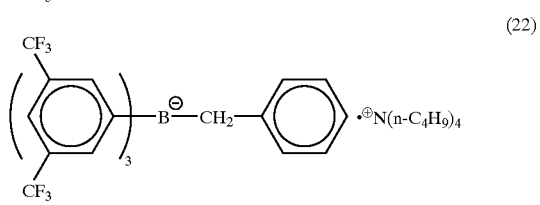
(22)
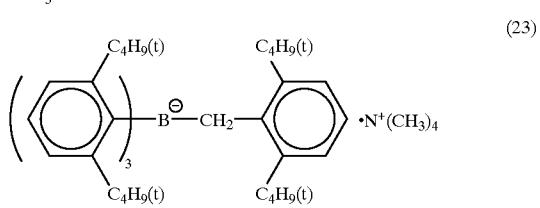
(23)
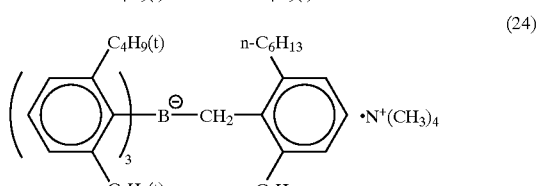
(24)
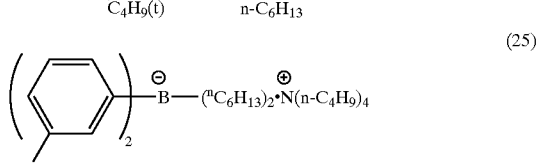
(25)
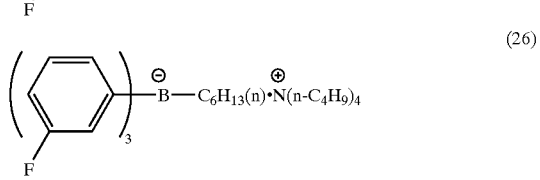
(26)
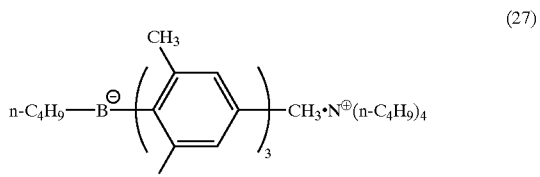
(27)
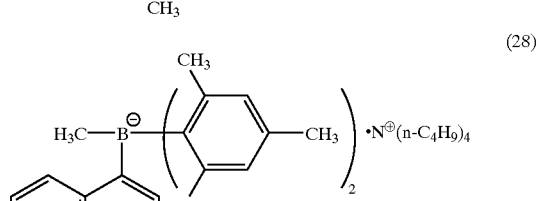
(28)
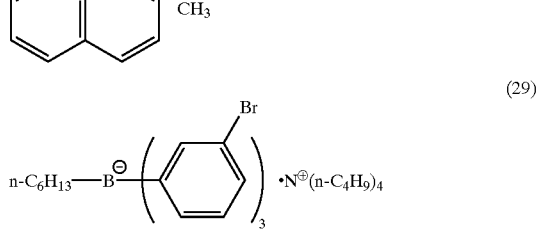
(29)

(30)
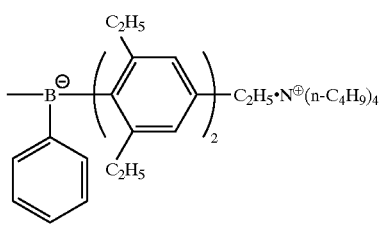
(31)
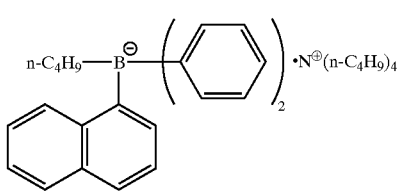
(32)
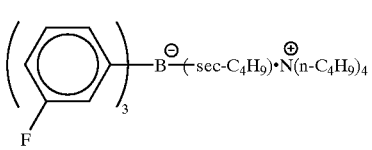
(33)
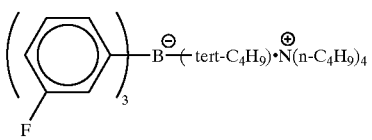
(34)
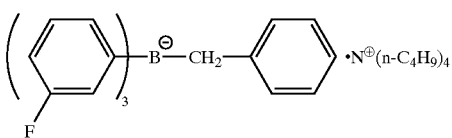
(35)
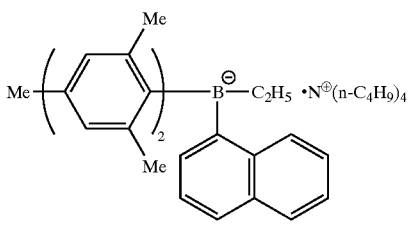
(36)
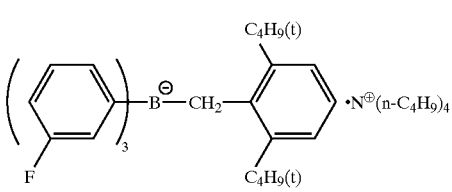
(37)
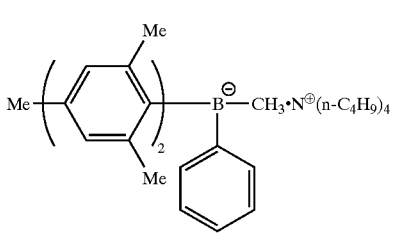
(38)
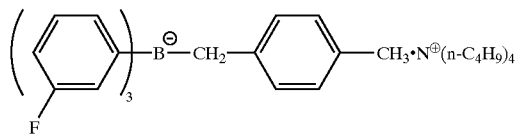
(39)
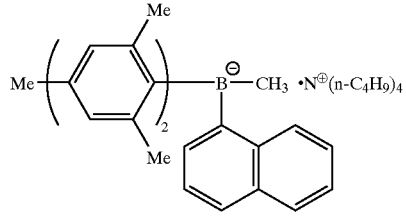
(40)
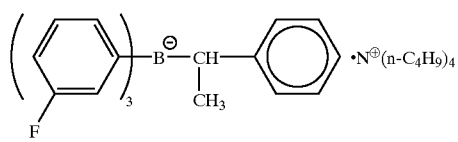
(41)
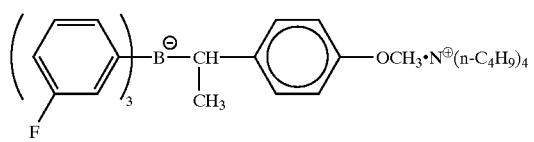
(42)
$(nC_4H_9)_4B^{\ominus}$  $\overset{\oplus}{N}(C_4H_9)_4$
(43)
$(nC_6H_{13})_4B^{\ominus}$  $\overset{\oplus}{N}(C_4H_9)_4$
(44)
$(isoC_4H_9)_4B^{\ominus}$  $\overset{\oplus}{N}(C_4H_9)_4$
(45)
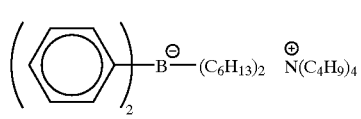
(46)
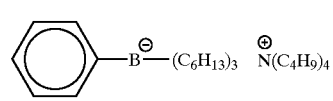
(47)
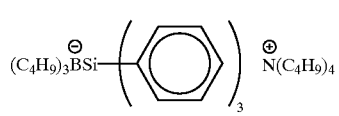
(48)
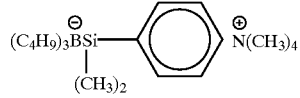

-continued (49)

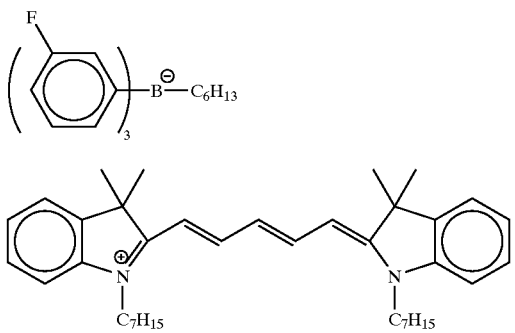

Dyes which are used in combination with the organic boronic compounds can be any of a catioinic dye, an anionic dye, and a nonionic dye. Preferably, they have absorption wavelengths whose maximum absorption wavelengths range from 300 to 1000 nm. A desired dye is selected arbitrarily from so-called spectral sensitized dyes whose maximum absorption wavelength is within the aforementioned range, and used for the purpose of adjusting photosensitive wavelengths to adapt to a light source to be used. As a result, a highly photosensitive image forming material can be obtained. Further, a light source having blue, green, and red colors, an infrared laser, or the like can be suitably selected.

For example, in a case in which a multicolor photosensitive and heat-sensitive image forming material which has an image forming layer in which monocolor photosensitive and heat-sensitive recording layers, which form color of different hues, are laminated to each other is used so as to form a color image, a spectral sensitized dye having different absorption wavelengths is contained in each of the monocolor photosensitive and heat-sensitive recording layers, which each forms color of a different hue, and light sources corresponding to absorption wavelengths of the spectral sensitized dyes are used. Accordingly, even if an image forming material having a laminated structure is used, since an image with high sensitivity and with high sharpness can be formed in each layer (each color), the multicolor image forming material as a whole succeeds in forming an image with high sensitivity and high sharpness.

When the image forming material of the present invention is used as a photo- and pressure-sensitive paper, the image forming material can be formed in such a laminated structure as described above, or the spectral sensitized dyes which together form multiple colors, the organic boron compounds, and the dye precursor which will be described later can be contained in the same layer. A more detailed description of a structure of the image forming layer will be given later.

Examples of the spectral sensitized dyes include: a keto dye such as a known coumarin (including ketocoumarin or sulfonylcoumarin) dye, a melostyryl dye, an oxonol dye, or a heimoxonol dye; a non-keto dye such as a non-keto polymethine dye, a triarylmethan dye, a xanthene dye, an anthracene dye, a rhodamine dye, an acridine dye, an aniline dye, or an azo dye; a non-keto polymethine dye such as an azomethine dye, a cyanine dye, a carbocyanine dye, a dicarbocyanine dye, a tricarbocyanine dye, a hemicyanine dye, or a styryl dye; a quinoneimine dye such as an azine dye, an oxazine dye, a thiazine dye, a quinoline dye, or a thiazole dye. Specific examples of these spectral sensitized dyes are disclosed in JP-A Nos. 62-143044, 3-20260, 1-84245, 1-138204, 1-100536, and 9-188686, and Japanese Patent Application National Publication (Laid-Open) No. 6-505287.

Preferably, a ratio of the dyes to the organic boron compounds used ranges from 1/0.1 to 1/100, and more preferably, from 1/0.5 to 1/10.

(A Dye Precursor Which Can Form Color Through Contact with a Base)

A dye precursor which can form color through contact with a base (in some cases, hereinafter, simply referred to as a 'dye precursor') means a compound which is colorless and whose protective group is eliminated in the presence of a base at room temperature or within a range of temperatures at which it is impossible for the dye precursor to form color without the base even if the dye precursor is heated, thus forming color dye. As dyes which are formed, any dyes that are able to form conjugation systems by azo, imino, or methine bond can be used. Examples of these dyes include an azo dye, an azomethine dye (including an indoaniline dye and an indophenol dye), an azine dye, an indigo-based dye, a quinone-based dye, a stilbene-based dye, a quinophthalone-based dye, an isoindolinone-based dye, a phthalocyanine-based dye, and the like. Dye precursors have protective groups at positions where the conjugation systems are cut.

The dye precursors in that substantially colorless leuco dyes in azomethine dyes known as a silver salt photographic system or azo dyes known as a transferring system, are substituted by protective groups so as to form color through contact with bases are more preferable, since various hues are selectable.

The azo dye is what is known as a dye produced from a diazonium salt and a coupler compound, and the azomethine dye is what is known as a dye produced from a developing agent and a coupler compound.

As an example of the diazonium salt, an aromatic and heterocyclic diazonium salt that is generally known can be used. In the case of diazonium salts having substituents, these substituents can be electron attractive groups or electron donative groups, the diazonium salt used can be arbitrarily selected in accordance with types of couplers to be used, absorption wave length of the desired azo dyes and light-fastness of the desired image forming material. For example, compounds which are disclosed in "Diazo Chemistry" (by Zolinger), "THE AROMATIC DIAZO-COMPOUNDS AND THEIR TECHNICAL APPLICATIONS" (by Sanders) and in Japanese Patent Application No. 9-260336 are known.

As examples of the developing agents, phenylenediamines, hydroquinones, and heterocyclic compounds which are generally known can be used. These developing agents can be arbitrarily selected in accordance with absorption wave length of the desired azo dyes and light-fastness of the desired image forming material. For example, compounds described in "THE THEORY OF THE PHOTOGRAPHIC PROCESS" (by James) are known.

Examples of the couplers are the same as those in the description of the substituent Cp in the formula (1) and in the formula (2) in the first embodiment of the present invention. Of course, the present invention is not limited to these examples.

In the same manner as the first embodiment of the present invention, in the second embodiment of the present invention, dye precursors which form color through contact with a base, at room temperature, or within a range of temperature at which it is impossible for the dye precursor to form color without the base even if the dye precursors are heated, are used. In order to increase a reaction rate of this color formation, an oxidizer can be used in combination with the dye precursors in the same manner as described in the first embodiment of the present invention.

As a dye precursor which can form color through contact with a base, the dye precursor A represented by the formula (1) or the dye precursor B represented by the formula (2) in the first embodiment of the present invention are particularly preferable.

(Base or Base Precursor)

As the base or the base precursor, a wide range of bases which allow the dye precursors used in combination to form color, or base precursors which generate such bases can be used. As examples of the bases, organic bases such as primary to tertiary amines, piperidines, piperazines, amidines, formamidines, pyridines, guanidines, and morpholines can be preferably listed.

Here, in addition to a base in a narrow sense of the term, "base" refers to a base in a wide sense of the term, which includes nucleophiles (Lewis base).

Specific examples of these organic bases include: piperazines such as N,N'-bis(3-phenoxy-2-hydroxypropyl)piperazine, N,N'-[bis[3-(p-methylphenoxy)-2-hydroxypropyl]piperazine, N,N'-bis[3-(p-methoxyphenoxy)-2-hydroxypropyl]piperazine, N,N'-bis(3-phenylthio-2-hydroxypropyl)piperazine, N,N'-bis[-3(β-naphthoxy)-2-hydroxypropyl]piperazine, N-3-(β-naphthoxy)-2-hydroxypropyl-N'-methylpiperazine, and 1,4-bis{[3-(N-methylpiperadino)-2-hydroxy]propyloxy}benzene; morpholines such as N-[3-(β-naphthoxy)-2-hydroxy]propylmorpholine, 1,4-bis[(3-morpholino-2-hydroxy)propyloxy]benzene, and 1,3-bis[(3-morpholino-2-hydroxy)propyloxy]benzene; piperidines such as N-(3-phenoxy-2-hydroxypropyl)piperidine and N-dodecylpiperidine; -triphenylguanidine, tricyclohexylguanidine, dicyclohexylphenylguanidine, 2-N-methyl-N-benzylaminoethyl 4-hydroxybenzoate, 2-N,N-di-n-butylaminoethyl 4-hydroxybenzonate, 4-(3-N,N-dibutylaminopropoxy)benzensulfonamide, 4-(2-N,N-dibutylaminoethoxycarbonyl)phenoxy acetate amide, trioctylamine, octhadecylamine, N-methyl-N-octadecylamine, and the like. A base can be used singly or two bases or more can be used in combination.

These bases are disclosed in JP-A Nos. 57-123086, 60-49991, 60-94381, 09-071048, 09-077729, and 09-077737.

A base precursor refers to a compound which frees a base under heating. As an example of such a compound, a salt of a base and organic acid, or the like can be listed. As the base which structures the base precursor, the examples listed for the above-described base are preferable. As the organic acid, it is possible to use Bronsted acid or Lewis acid, which are generally used. It is also possible to use carboxylic acid which releases the base through a decarboxylation reaction. Sulfonylacetatic acid and propiolic acid are particularly preferable because they make it easy for the decarboxylation reaction to occur. Further, it is preferable that the aforementioned sulfonylacetic and propiolic acid have aromatic substituents (aryl groups or unsaturated heterocyclic groups) to further promote the decarboxylation reaction. Specific examples of a base precursor that is a salt of sulfonylacetatic acid are disclosed in JP-A No. 59-168441, and examples of a base precursor that is a salt of propiolic acid are disclosed in JP-A No. 59-180537.

Examples of diacidic base precursors which are able to release amidine or guanidine as a base are described below. However, the second embodiment of the present invention is not limited to this.

BP-1
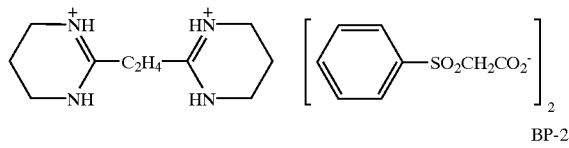

BP-2
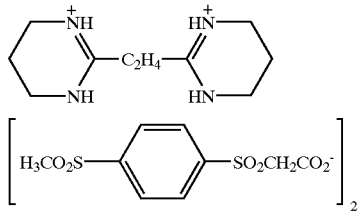

BP-3
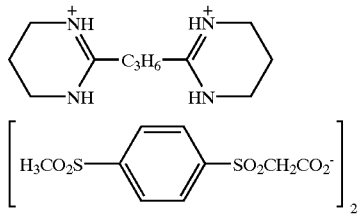

BP-4
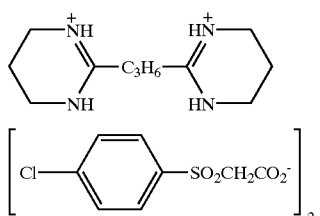

BP-5
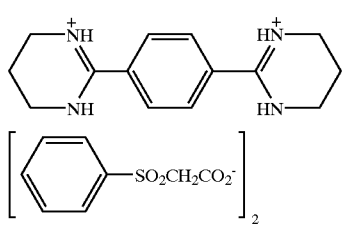

BP-6
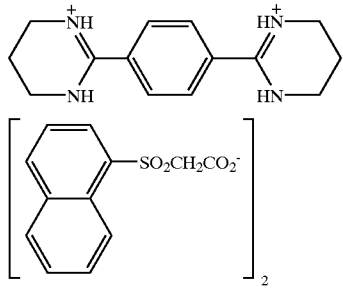

BP-7
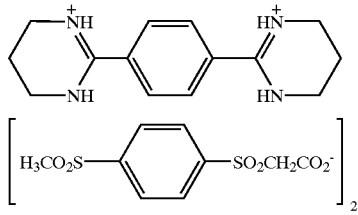

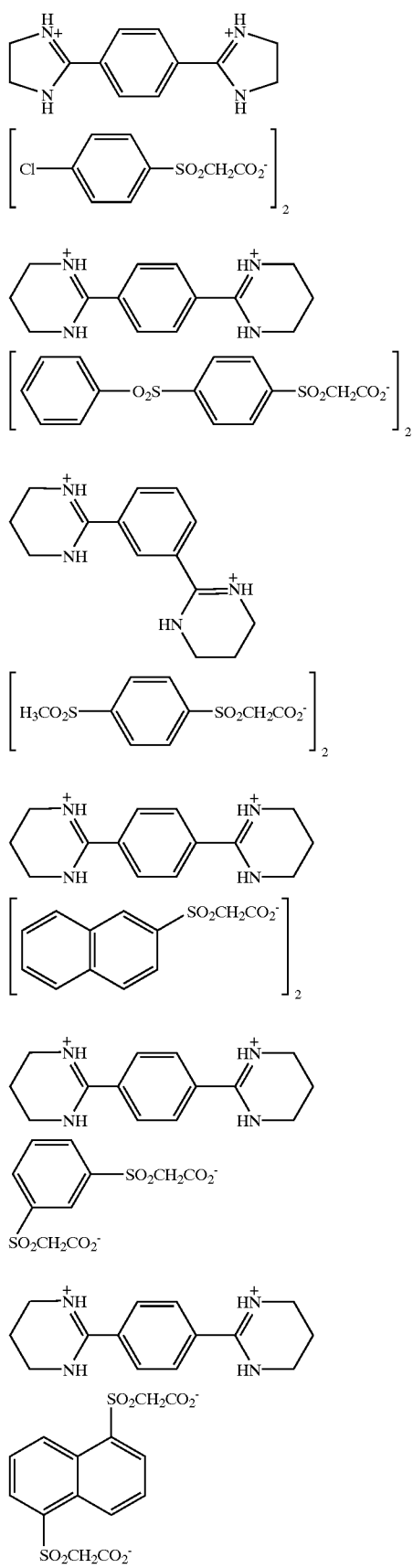
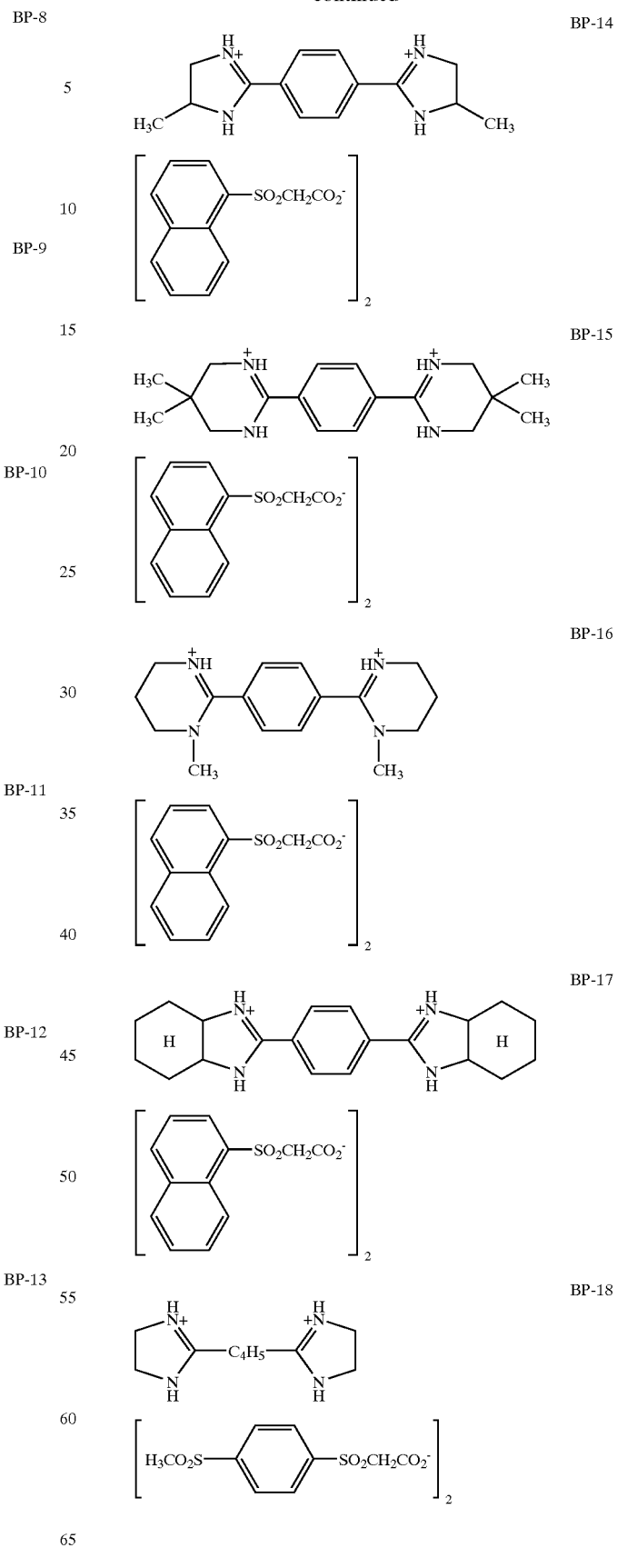

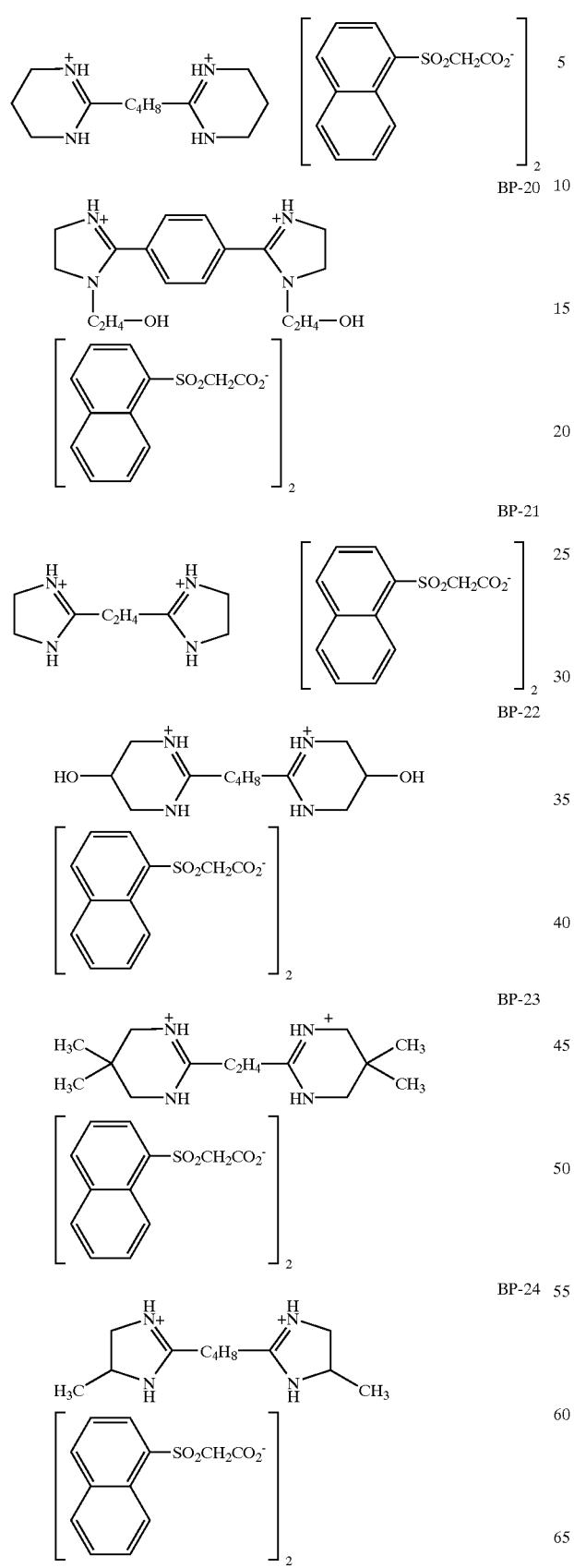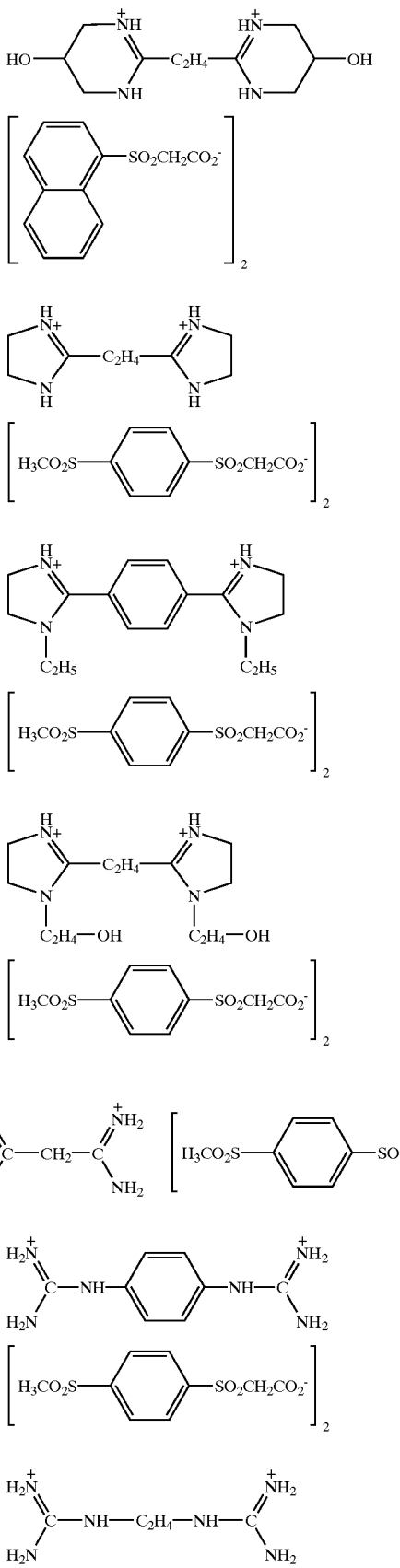

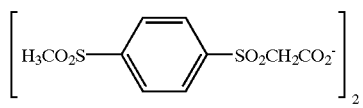
BP-32

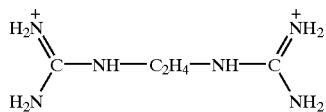
BP-33

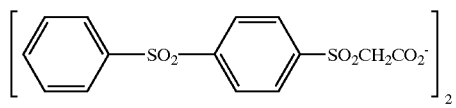
BP-34

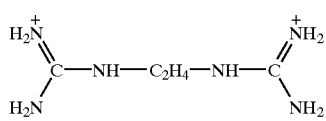
BP-35

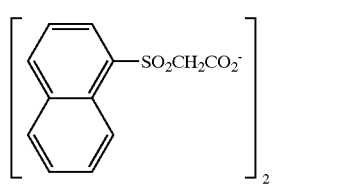
BP-36

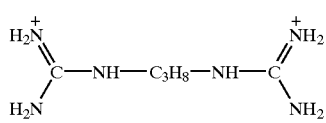
BP-37

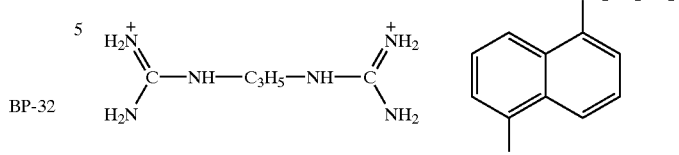
BP-38

BP-39

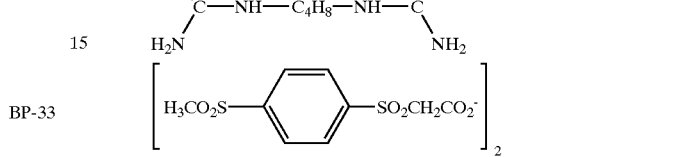
BP-40

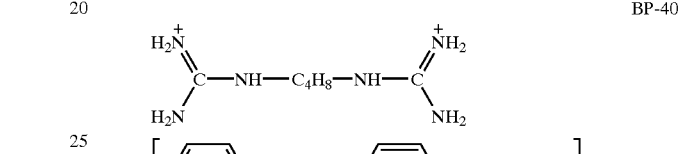
BP-41

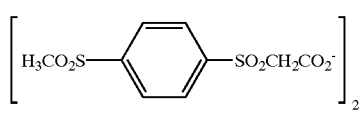

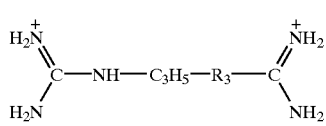

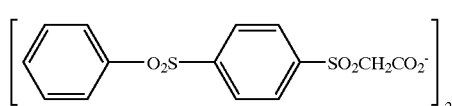

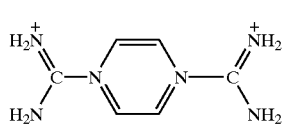

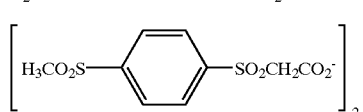

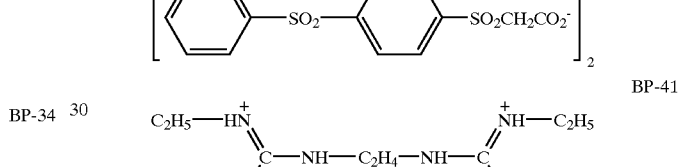

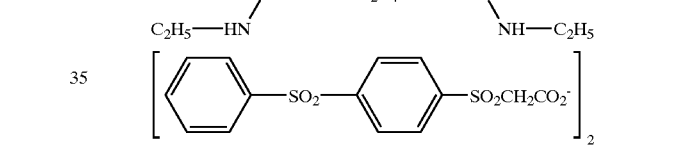

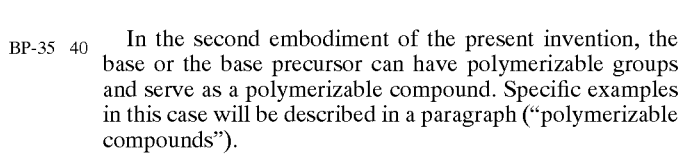

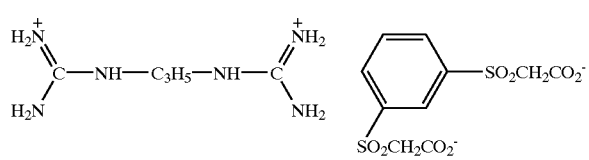

In the second embodiment of the present invention, the base or the base precursor can have polymerizable groups and serve as a polymerizable compound. Specific examples in this case will be described in a paragraph ("polymerizable compounds").

The content (mol) of the base or the base precursor in an image forming layer (recording layer) is preferably 0.1 to 100 times, and more preferably, 0.5 to 30 times, of the content of dye precursors. However, since the range of the preferable content of the base or the base precursor varies in accordance with the dye precursor used in combination with the base or the base precursor, it is not limited to the aforementioned range.

(Polymerizable Compound)

The polymerizable compound is a compound which has at least one ethylenic unsaturated bond in its chemical structure. Monomers, prepolymers such as a dimer and a trimer of a monomer, oligomers, a mixture thereof, and a copolymer thereof and the like are included. Examples of these compounds include unsaturated carboxylic acid and its salt, an ester generated by the unsaturated carboxylic acid or its salt reacting with a fatty polyvalent alcohol compound, and an amide formed by the unsaturated carboxylic acid and its salt reacting with a fatty polyvalent amine compound.

Examples of the unsaturated carboxylic acid include acrylic acid, methacrylic acid, itaconic acid, crotonic acid, isocrotonic acid, maleic acid, and the like. Examples of salts of the unsaturated carboxylic acid include sodium salt and potassium salt, of the aforementioned carboxylic acid.

Specific examples of esters generated by reaction between a fatty polyvalent alcohol compound and the unsaturated carboxylic acid, include: acrylic acid esters such as ethylenelglycol diacrylate, triethyleneglycol triacrylate, 1,4-butanediol diacrylate, tetramethyleneglycol diacrylate, propyleneglycol diacrylate, trimethylolpropane triacrylate, trimethylolethane triacrylate, 1,6-cyclohexanediol diacrylate, tetraethyleneglycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, sorbitol triacrylate, sorbitol tetraacrylate ,sorbitol pentaacrylate, sorbitol hexaacrylate, polyester acrylate oligomer, and the like;

methacrylic acid ester such as tetramethyleneglycol dimethacrylate, triethyleneglycol methacrylate, trimethylolpropane trimethacrylate, trimethylolethane trimethacrylate, ethyleneglycol dimethacrylate, 1,4-butanediol dimetharylate, pentaerythritol dimethacrylate, pentaerythritol trimethacrylate, dipentaerythritol dimethacrylate, sorbitol trimethacrylate, sorbitol tetramethacrylate, bis-[p-(3-methacryloxy-2-hydroxypropoxy) phenyl]dimethylmethane, bis-[p-(acryloxyethoxy) phenyl]dimethylmethane, and the like;

itaconic acid ester such as ethyleneglycol itaconate, propyleneglycol diitaconate, 1,2-butandiol diitaconate, 1,4-butandiol diitaconate, tetramethyleneglycol diitaconate, pentaerythritol diitaconate, sorbitol tetraitaconate, and the like;

crotonic acid ester such as ethyleneglycol dicrotonate tetramethyleneglycol dicrotonate, pentaerythritol dicrotonate, sorbitol tetracrotonate, and the like;

isocrotonic acid ester such as ethyleneglycol diisocrotonate, pentaerythritol diisocrotonate, sorbitol tetraisocrotonate, and the like;

maleic acid ester such as ethyleneglycol dimarate, triethyleneglycol dimalate, pentaerithritol dimalate, soribitol tetramalate and the like; and the aforementioned mixtures of the aforementioned esters.

Specific examples of amides generated by reaction between a fatty polyvalent amine compound and the unsaturated carboxylic acid, include methylenebis-acrylamide, methylenebis-methacrylamide, 1,6-hexamethylenebis-acrylamide, 1,6-hexamethylenebis-methacrylamide, diethylenetriamine trisacrylamide, xylenebisacrylamide, xylenebismethacrylamide, and the like.

As another example, a vinylurethane compound which has two types of polymerizable vinyl groups or more in a molecule and in which a vinyl monomer containing a hydroxy group represented by the following formula is added to a polyisocyanate compound which has two types of isocyanate groups or more in a molecule, and which is described in Japanese Patent Application Publication (JP-B) No. 48-41708 can be listed. Moreover, in the following formula, $R^{81}$ and $R^{82}$ each represents a hydrogen atom or a methyl group.

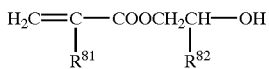

High polymer compounds having vinyl groups or vinylidene groups such as condensation products, high polymer compounds having a hydroxy group, an amino group, an epoxy group, a halogen atom, a sulfonyloxy group at side chains thereof, and acrylic acid, methacrylic acid, or polymers of acrylic acid and/or methacrylic acid can be used in the present invention.

Further, compounds having a vinyl group in a molecule of a color image forming substance such as a dye or a leuco dye can be used as a polymerizable compound.

In the second embodiment of the present invention, as described above, the base or the base precursor may have polymerizable groups may function as the polymerizable compound. When the image forming material containing such base or base precursor is irradiated with light imagewisely, a radical forming agent in a light-irradiated portion is decomposed so as to generate radicals. With these radicals, the base or the base precursor as the polymerizable compound carries out a polymerization reaction, and is hardened. As a result, after the image forming material is irradiated with light, even if this image forming material is heated or pressurized, the base in the light-irradiated portion (which base may be a base generated by a base precursor) does not contact with and react with the dye precursor, and so the dye precursor does not form color. On the other hand, the base in a non-irradiated portion (which base may be a base generated by the base precursor) is diffused through application of heat and/or pressure, and contacts with and reacts with the dye precursors so that the dye precursor forms color. Accordingly, the non-irradiated portion forms color, and the light-irradiated portion is kept white.

As examples of bases having polymerizable groups, organic bases having polymerization groups (such as ethylene groups) in molecules such as a tertiary amine, piperidines, piperazines, amidines, formamidines, pyridines, guanidines, and morpholines can be listed. Specific examples of these bases include compounds in which the organic bases listed in the first embodiment of the present invention are substituted, directly or through connection groups, by a polymerizable ethylene group, a (metha) acryl group or a (metha) acrylamide group. Further, specific examples of base precursors having polymerizable groups include compounds in which the base precursors listed in the first embodiment of the present invention are substituted, directly or through connection groups, by a polymerizable ethylene group, a (metha) acryl group, or a (metha) acrylamide group.

Specific examples of bases or base precursors having polymerizable groups which are suitably used are shown as follows. However, the second embodiment of the present invention is not limited to these examples.

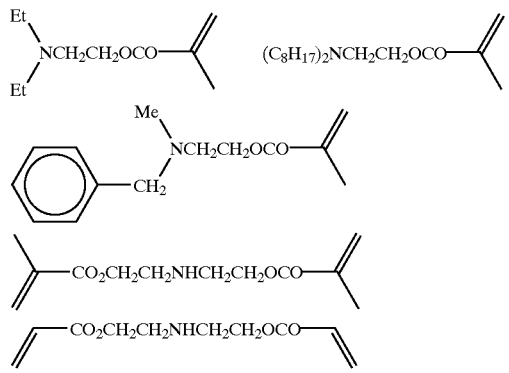

-continued

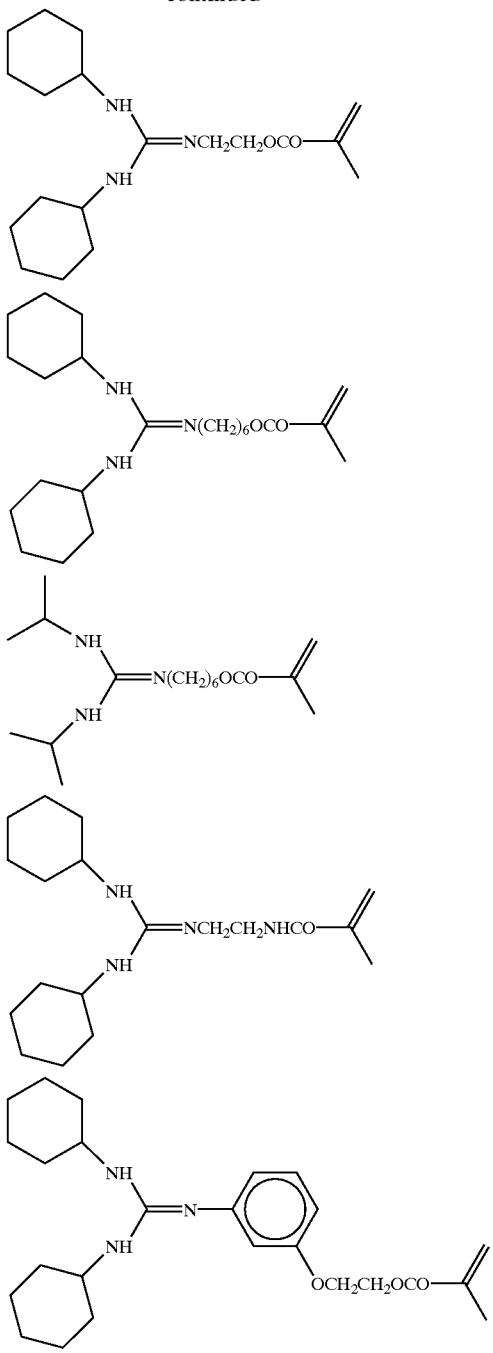

Hardening of the bases or the base precursors having polymerizable groups can be promoted by adding other polymerizable compounds to the bases or the base precursors. Examples of other polymerizable compounds include the compounds listed as the aforementioned polymerizable compounds.

(Other Structural Components)

In the image forming material according to the second embodiment of the present invention, other than oxidants that can be used in combination with the aforementioned dye precursors, a color forming assistant can be added for the purpose of promoting the color-forming reaction.

Examples of the color forming assistants include substances for increasing density of the formed color during an image recording process by application of heat or pressure, or substances for decreasing a minimum color-forming temperature. More specifically, the color forming assistant is used in order to create circumstances under which the dye precursors and the bases can easily react with each other, due to decreasing melting points of the dye precursors or the bases, stabilizing emulsions, or decreasing softening points of microcapsule walls.

Examples of the color forming assistants that can be used for the second embodiment of the present invention include phenol derivatives, naphthol derivatives, alkoxy substituted benzenes, alkoxy substituted naphthalenes, aromatic ether, thioether, ester, amide, ureide, urethane, sulfonamide, compounds containing carboxyl or hydroxy group which help to form an image in the image forming layer in cases with low energy.

In addition, oxygen scavengers, reducing agents such as chain transfer agents of active hydrogen donor, or other compounds which promote polymerization in a chain transferring manner to a photopolymerizable composition for the image forming material of the present invention so as to promote polymerization.

Examples of the oxygen scavengers include phosphine, phosphonate, phosphite, or other compounds which are easily oxidized by reacting with oxygen.

Specific examples of these include N-phenylglycine, trimethylbarbituric acid, N,N-dimethyl-2,6-diisopropylaniline, and N,N-2,4,6-pentamethylaniline. Compounds such as thiols, thioketones, trihalomethyl compounds, lophine dimer compounds, iodonium salts, sulfonium salts, adinium salts, organic peroxides, diazonium salts, and quinonediazides are effective as polymerization accelerators.

(Microcapsule)

Either the dye precursor which can form color through contact with a base or the base or the base precursor is preferably contained in microcapsules. As a method of producing the microcapsules, conventionally known methods can be adopted. Examples of these methods include: a method which utilizes a coacervation of a hydrophilic wall forming material and which is disclosed in U.S. Pat. Nos. 2,800,457 and 2,800,458; an interfacial polymerization method disclosed in U.S. Pat. No. 3,287,154, G. B. Patent No. 990443, and JP-B Nos. 38-19574, 42-446, and 42-771; a method using polymer precipitation disclosed in U.S. Pat. Nos. 3,418,250 and 3,660,304; a method using an isocyanate polyol wall forming material disclosed in U.S. Pat. No. 3,796,669; a method using an isocyanate wall forming material disclosed in U.S. Pat. No. 3,914,511; a method using a urea-formaldehyde-based or ureaformaldehyde-resorcinol-based wall forming material disclosed in U.S. Pat. Nos. 4,001,140, 4,087,376, and 4,089,802; a method using a wall forming material such as a melamine-formaldehyde resin or a hydroxypropyl cellulose disclosed in U.S. Pat. No. 4,025,455; an in situ method through monomer polymerization disclosed in JP-B No. 36-9168 and JP-A No. 51-9079; an electrolytic dispersing and cooling method disclosed in G. B. Patent Nos. 952807 and 965074; a spray drying method disclosed in U.S. Pat. No. 3,111,407 and G. B. Patent No. 930422; or methods disclosed in JP-B No. 7-73669, JP-A Nos. 4-101885 and 9-263057.

The method of producing the microcapsules is not limited to these examples. However, it is particularly preferable to adopt a method using interfacial polymerization in which dye precursors are dissolved or dispersed in a hydrophobic organic solvent which forms capsule core materials to prepare an oil phase, and the oil phase is mixed with an aqueous phase in which a water-soluble high polymer is dissolved, emulsified and dispersed by means of a homogenizer or the like, and then the obtained solution is heated to cause a high polymer forming reaction at the interface of oil droplets so as to form the microcapsule walls formed with high polymer substances. By this method, microcapsules whose particle diameter is uniform can be formed in a short period of time. As a result, an image forming material which is excellent in storage stability can be obtained.

Reactants which form high polymers are added to inside and/or outside of the oil droplets. Specific examples of the high polymer include polyurethane, polyurea, polyamide, polyester, polycarbonate, urea-formaldehyde resin, melamine resin, polystyrene, styrene-methacrylate copolymer, and styrene-acrylate copolymer. Among these, polyurethane, polyurea, polyamide, polyester, and polycarbonate are preferable, and polyurethane and polyurea are particularly preferable. Two or more of the aforementioned high polymers can be used in combination.

Examples of the aforementioned water soluble high polymers include gelatin, polyvinyl pyrolidone, and polyvinyl alcohol. For example, in a case in which polyurethane is used as the capsule wall material, polyvalent isocyanate and a second substance (e.g., polyol or polyamine) which reacts with the polyvalent isocyanate so as to form a capsule wall are mixed with an aqueous solution of water soluble high polymer (aqueous phase) or an oil medium (oil phase) to be encapsulated, and the oil phase is emulsified in the water phase. Thereafter, the resultant emulsion is heated so as to cause a high polymer forming reaction at the interface of the oil droplets and the aqueous phase, and a microcapsule wall can be formed.

Examples of the polyvalent isocyanate and the polyol or polyamine that reacts with the polyvalent isocyanate disclosed in U.S. Pat. Nos. 3,281,383, 3,773,695, 3,793,268, and JP-B Nos. 48-40347, and 49-24159, JP-A Nos. 48-80191, and 48-84086, and those described in "Polyurethane Resin Handbook" (written by Keiji Iwata, Nikkan Industrial Press Co., Ltd. (1987)) can be used.

When a microcapsule containing dye precursors is prepared, the dye precursor can be dissolved in a solvent or can be in solid form in the solvent. Solvents (oil mediums) can generally be arbitrarily selected from high boiling point oils. Examples of the high boiling point oils include: phosphate ester, phthalate ester, acrylate ester, methacrylate ester, carboxylate ester, fatty acid amide, alkylated biphenyl, alkylated terphenyl, chlorinated paraffin, alkylated naphthalene, diallylethane, compounds that are solid at room temperature, oligomer oil, polymer oils, and the like. Specifically, those disclosed in JP-A Nos. 60-242094 and 62-75409 can be used. However, during encapsulation, these solvents do not have to be used.

In cases where a dye precursor is dissolved in the solvent contained in microcapsules, the solution containing the dye precursor can be encapsulated. In this case, preferably, the solvent is used in an amount of 1 to 500 parts by weight based on 100 parts by weight of the dye precursor. In a case in which the dye precursor to be contained in the microcapsules has low solubility in the aforementioned solvent or in a case in which the aforementioned solvent is not used, a low boiling point solvent in which the dye precursor is easily dissolved can be used in combination as an aid. Examples of the low boiling point solvent include ethyl acetate, propyl acetate, isopropyl acetate, butyl acetate, and methylene chloride.

On the other hand, an aqueous solution in which a water soluble high polymer is dissolved is used for the aqueous phase. The aforementioned oil phase is added to this aqueous solution, and thereafter, is emulsified by means of a homogenizer or the like. The water soluble high polymer allows this dispersion to be performed homogeneously and easily, and acts as a dispersion medium which stabilizes the emulsion. In order to form a more homogeneous emulsion, and stabilize the emulsion, further, a surfactant can be added to at least one of the oil phase and the aqueous phase. As the surfactant, known active surfactants for emulsifying can be used.

As described above, the method of producing microcapsules has been explained by using examples of encapsulating dye precursors in the microcapsules. However, as described above, in the second embodiment of the present invention, the base or the base precursor may be contained in microcapsules. In that case, the same method as described above is used.

When the dye precursor, or the base or the base precursor is encapsulated in the microcapsules, a mean particle diameter of the microcapsules is preferably less than or equal to 20 $\mu$m, and more preferably, less than or equal to 7 $\mu$m from a viewpoint of obtaining an image with high resolution. On the other hand, when the microcapsules thus produced are too small, the total surface area of the microcapsules becomes large compared with larger microcapsules when the amount of the microcapsules is constant, and a large amount of the capsule wall agent must be used. Accordingly, the mean particle diameter of the microcapsule is preferably more than or equal to 0.1 $\mu$m.

Among the image forming materials according to the second embodiment of the present invention in a case of using the microcapsules, in the image forming materials of a heat-sensitive type, substances permeate through the microcapsule walls during heating. At this time, since the microcapsules are not broken, the heat-sensitive image forming material can form color inside the microcapsule or at portions closest to the microcapsule. As a result, the heat-sensitive image forming material is excellent in terms of degree of image graininess.

Among the image forming materials according to the second embodiment of the present invention in the case of using a microcapsule, in the image forming materials of a pressure-sensitive type, the microcapsules are broken thus enabling substances contained in the microcapsule to disperse outside thereof. Accordingly, the image forming material of the pressure-sensitive type forms an image having more blots than the image forming material of the heat-sensitive type. As a result, in view of sharpness and blotting of an image, the image forming material of the (photosensitive and) heat-sensitive type is more preferable than the (photosensitive and) pressure-sensitive material.

(Specific Structure of an Image Forming Layer)

The image forming material according to the second embodiment of the present invention includes at least one type of each of the aforementioned photopolymerization initiator, the dye precursor which forms color through contact with a base, the base or the base precursor, and the polymerizable compound is contained in the image forming layer. Each of these components is encapsulated in microcapsules if necessary, and then dissolved, emulsified or dispersed in an appropriate solvent in combination with a binder and various types of additive agents which are added as needed so that a coating solution is prepared. The obtained coating solution is applied onto a support by using a known application method, and then dried so that the image forming layer is formed.

When the image forming material according to the second embodiment of the present invention is used as a multi-color image forming material, generally, the image forming layer is structured such that a plurality of photosensitive image recording layers having different hues are laminated on the support. In this case, each photosensitive recording layer contains microcapsules containing a dye precursor, a photopolymerization initiator and other main components, and the hue formed by each dye precursor is different from those formed by the other dye precursors. However, the image forming layer may comprise only one layer which contains the microcapsules containing two dye precursors or more each forming color of a different hue, the two photopolymerization initiators or more, and each of the other main components (of course, the component contained in the microcapsule may be the base or the base precursor). When this image forming material is irradiated with light, it is exposed by light of the light source having different wavelengths, thus forming a multicolor image.

In a case in which a plurality of photosensitive recording layers having different hues are laminated, an intermediate layer containing a filter dye can be disposed between each of the monocolor photosensitive layers.

The intermediate layer is mainly structured by a binder, and it can contain an additive agent such as a hardening agent, a polymer latex, a mica, or a UV absorbent, as needed. When the filter dye is used, it can be selected from the aforementioned spectral sensitizing compounds. However, in view of forming an image which is excellent in sharpness, preferably, the filter dye has the same light absorbing wavelength as that of the spectral sensitizing compound contained in the photosensitive layer which is disposed immediately above the intermediate layers containing the filter layer.

The aforementioned filter dye may be emulsified through an oil droplet-in-water dispersion method or a polymer dispersion method, and it can be added to a desired layer, especially to the intermediate layer.

In the oil droplet-in-water dispersion method, the filter dye is dissolved in a single solution which is one of a high boiling point solvent whose boiling point is 175° C. or above and a low boiling point solvent whose boiling point ranges from 30 to 160° C. or in a mixture thereof, and thereafter, the obtained solution is finely dispersed in an aqueous solution such as water, an aqueous gelatin solution, or an aqueous polyvinyl alcohol solution in the presence of a surfactant.

As an example of the high boiling point solvent, a solvent disclosed in U.S. Pat. No. 2,322,027 can be listed. As a high boiling point solvent and a co-solvent, it is possible to use the same solvents as those used in the above-described method of producing microcapsules.

Further, dispersion of the filter dye can be followed by phase transition. Namely, the intermediate layer may be applied after the co-solvent is removed or reduced from the filter dye or reduced through distillation, Nuder washing or ultrafiltration.

Specific examples of processes of a method of dispersing polymers, and latexes for hardening and impregnation polymers are disclosed in U.S. Pat. No. 4,199,383, German Patent (OLS) Nos. 2541274 and 2541230, JP-A Nos. 49-74538, 51-59943, and 54-32552, and "Research Disclosure, Vol. 148" (August. 1976, Item: 14850).

As examples of the latexes, copolymer latexes of acrylic acid ester or methacrylic acid ester such as ethyl acrylate, n-butyl acrylate, n-butyl methacrylate, or 2-acetoacetoxyethyl methacrylate; copolymer latexes of acid monomers such as acrylic acid, 2-acrylamide-2-methylpropanesulfonic acid or the like.

A layer containing a polymer such as gelatin, PVA, or the like which blocks permeation of oxygen can be disposed between the support and the photosensitive layer (image forming layer). By forming such a layer, it is possible to prevent color-fading of image due to oxidation.

A so-called halation inhibiting layer can also be disposed between the support and the photosensitive layer, or on the side of the support opposite the side having the photosensitive layer in a case of a transparent support. In this case as well, in view of increasing whiteness of a background portion, preferably, the halation inhibiting layer can be bleached through light irradiation or heating. When the halation inhibiting layer is bleached through light irradiation, a dye and a boron compound can be used in combination, for example. When the halation inhibiting layer is bleached through heating, methods of bleaching dyes by bases or nucleophilic agents can be used, for example.

In the image forming material according to the second embodiment of the present invention, for the purpose of improving color-fastness of the image with respect to light and heat or of reducing yellowing of the image due to light irradiation after image fixation, known antioxidants described below are preferably used.

Examples of such antioxidants are disclosed in European Patent Laid-Open Nos. 223739, 309401, 309402, 310551, 310552, and 459416, German Patent Laid-Open No. 3435443, JP-A Nos. 54-48535, 62-262047, 63-113536, 63-163351, 2-262654, 2-71262, 3-121449, 5-61166, 5-119449, and U.S. Pat. Nos. 4,814,262 and 4,980,275.

Further, in the image forming layer of the image forming material according to the second embodiment of the present invention, using various known additives which are already used in heat-sensitive recording materials and pressure-sensitive recording materials is also effective. Specific examples of these antioxidants are disclosed in JP-A Nos. 60-107384, 60-107383, 60-125470, 60-125471, 60-125472, 60-287485, 60-287486, 60-287487, 60-287488, 61-160287, 61-185483, 61-211079, 62-146678, 62-146680, 62-146679, 62-282885, 63-051174, 63-89877, 63-88380, 63-088381, 63-203372, 63-224989, 63-251282, 63-267594, 63-182484, 01-239282, 04-291685, 04-291684, 05-188687, 05-188686, 05-110490, 05-1108437, 05-170361, and JP-B Nos. 48-043294, and 48-033212.

As examples of binders used in the image forming layer in the image forming material according to the second embodiment of the present invention, known water soluble high polymer compounds or latexes can be used. Examples of the water soluble high polymer compounds include methyl cellulose, carboxymethyl cellulose, hydroxyethyl cellulose, hydroxypropyl cellulose, starch derivatives, casein, gum arabic, gelatin, ethylene-maleic anhydride copolymer, styrene-maleic anhydride copolymer, polyvinyl alcohol, epichlorohydrine modified polyamide, isobutylene-maleic anhydride-salicylic acid copolymer, polyacrylic acid, polyacrylamide, and modified polymers thereof. Examples of latexes include styrene-butadiene rubber latex, methyl acrylate-butadien rubber latex, vinyl acetate emulsion, and the like.

As pigments which can be used for the image forming material according to the second embodiment of the present invention, any of known organic or inorganic pigments can be used. Specific examples of these include kaolin, burning kaolin, talc, agalmatolite, diatomaceous earth, calcium carbonate, aluminum hydroxide, magnesium hydroxide, zinc oxide, lithopone, amorphous silica, coloidal silica, burning gypsum, silica, magnesium carbonate, titanium oxide, alumina, barium carbonate, barium sulfate, mica, microballoon, urea-formalin filler, polyester particles, cellulose filler, and the like.

In the image forming layer of the image forming material of the second embodiment of the present invention, various known additives such as a wax, an antistatic agent, a defoaming agent, a conductive agent, a fluorescent dye, a surfactant, and a UV absorbent, and precursors thereof can be used, as needed.

C: Protective Layer

In the image forming material according to the second embodiment of the present invention, a protective layer can be disposed on the image forming layer as needed. Two protective layers or more can be laminated as needed. Examples of materials used in the protective layer include: water soluble high polymer compounds such as polyvinyl alcohol, carboxy modified polyvinyl alcohol, vinyl acetate-acrylamide copolymer, silicon modified polyvinyl alcohol, starch, modified starch, methyl cellulose, carboxymethyl cellulose, hydroxymethyl cellulose, gelatine, gum arabic, casein, hydrolyzed product of styrene-maleic acid copolymer, half ester hydrolyzed product of styrene-maleic acid copolymer, isobutylene-maleic anhydride copolymer, polyacrylamide derivatives, polyvinyl pyrolidone, sodium polystyrene sulfonate, sodium alginate, and the like; and latexes such as styrene-butadiene rubber latex, acrylonitrile-butadiene rubber latex, methyl acrylate-butadiene rubber latex, and vinyl acetate emulsion. The water soluble high polymer compound contained in the protective layer may be crosslinked in order to improve stock stability of the image forming material. Specific examples of crosslinking agents include water soluble initial condensation products such as N-methylolurea, N-methylolmelamine, and urea-formaline, dialdehyde compounds such as glyoxal and glutaraldehyde, inorganic crosslinking agents such as boron and borax, and polyamide epichlorohydrin. The protective layer can be hardened by electron beams. Further, the protective layer can comprise known pigments, metallic soaps, waxes, surfactants, fluorescent whitening agents, and UV absorbents. Preferably, application amount of the protective layer ranges from 0.2 to 5 $g/m^2$, and more preferably, from 0.5 to 2 $g/m^2$. Preferably, film thickness of the protective layer ranges from 0.2 to 5 $\mu$m, and more preferably, from 0.5 to 2 $\mu$m.

[Image Forming Method]

An image forming method according to the second embodiment of the present invention will be explained hereinafter.

(A First Image Forming Method)

In the image forming material in which microcapsules are used in the image forming layer, an image can be formed by heating imagewisely and/or pressurizing the image forming layer. On the other hand, in a case in which the microcapsules are not used in the image forming layer and a dye precursor contained in the image forming layer does not form color at room temperature only through an action of a base or a base precursor, the image can be formed by heating the image forming layer imagewisely. Namely, the dye precursor of the image forming material according to the second embodiment of the present invention forms color through contact with the base, or through contact with the base together with heating, so that an image is formed. Being different from an image forming material using a dye precursor which forms color solely by heating, non-image areas of the image forming material according to the second embodiment of the present invention are not easily fogged. Therefore, the obtained image is subjected to an image fixation in the same manner as the fixation process in a second image forming method later described, thus being an image which is excellent in light-fastness.

(A Second Image Forming Method)

The image forming material according to the second embodiment of the present invention can form an image by a second image forming method which comprises a latent image forming process and a developing process. In the latent image forming process, the image forming layer is imagewisely irradiated with light which is absorbed by the photopolymerization initiator, and polymerization initiating species are generated at light-irradiated portions of the image forming layer to thereby polymerize polymerizable compounds contained in the layer so that a latent image is formed. In the developing process, the entire surface of the image forming layer is heated and/or pressurized so that the dye precursor contacts the base or base precursor in accordance with the obtained latent image so that an image is formed.

At this time, since light with which the image forming layer is irradiated during the latent image forming process only needs to be of an intensity at which the polymerization initiating species are generated by the photopolymerization initiator so as to polymerize the polymerizable compounds in the layer, high sensitivity and a high processing rate can be ensured by this second image forming method. Further, photopolymerization initiators corresponding to each of light wavelengths from UV to near-infrared rays can be selected. Namely, since light sources can be employed within a wide range of color-forming wavelengths, even when the image forming material is multi-colored, mixture of colors is not likey to be caused. Further, since it is possible to use inexpensive light sources, it is thereby possible to provide image forming methods by which images can be manufactured inexpensively.

A laser, an LED, a xenon light, a fluorescent lamp, a mercury lamp, a tungsten lamp, a metal halide lamp, or the like can be used as a light source. In accordance with the organic dyes used, light sources having two wavelengths or more can be used.

Light is usually irradiated from the image forming layer side of the image forming material. However, in a case in which a transparent support is used as the support of the image forming material, light can be irradiated from the support side of the image forming layer.

The upper limit of the heating temperature when the entire surface of the image forming layer is heated in the developing process is restricted to a temperature at which the dye precursor does not form color by itself in a state in which a base is not present together with the dye precursor. If the heating temperature is set to such a temperature, white portions (non-image area) of the image forming layer does not become fogged.

In a case in which the image forming layer is formed using microcapsules, conditions of application of heat and/or pressure to be applied to the entire surface of the image forming layer need only be that which suffices for the image forming materials to pass through the microcapsules or for the image forming materials to break the microcapsules ('breakage' in this case includes a state in which substances outside the microcapsules penetrate inside the microcapsules).

Conditions of specific temperature and/or pressure applied to the entire surface of the image forming layer and times can be appropriately set in accordance with types and densities of dye precursors, or of the bases or base precursors. When using the microcapsules, the conditions may be set in accordance with the capsule wall materials. Heating temperature is preferably from 50° C. to 180° C., and more preferably from 70° C. to 130° C. When the entire surface of the image forming layer is heated, as a heating source which can be used for heating the image forming layer, a heating roller, a heat-sensitive head, a thermal stamp, a near-infrared ray (laser), an infrared ray (laser), and the like can be listed as examples thereof.

In a case in which the obtained image for which the above-described developing process has been completed undergoes an image processing as is, it is not particularly necessary to have a fixation process in this second image forming method. However, in order to obtain an image with superior light-fastness, it is desired to carry out the fixation process in which images are fixed by irradiating the entire surface of the image forming layer with light after the developing process has been completed.

Due to this fixation process, it is possible to polymerize both image areas and non-image areas thus making it possible to obtain an excellent fixed image with superior light-fastness. Further, in a case in which dyes are contained in the image forming material as components of the photopolymerization initiator, the dye is bleached by such fixation process as described above so that fogging at background portions of non-image areas can be prevented. As a result, it is possible to obtain images with a higher degree of whiteness.

The light sources in the fixation process of this second image forming method are not used for writing images imagewisely but are used for being irradiated onto the entire surface of the image forming layer of the image forming material. Accordingly, even when high output light sources are used in the fixation process, inexpensive manufacture of the image forming material and increase of a processing rate are not hindered.

EXAMPLES

The present invention will next be described by way of examples which should not be construed as limiting the invention. In the following examples, % refers to percent by weight as long as it is not stated otherwise.

1. Preparation of Dye Precursor-containing Microcapsule Dispersion Solution 1-a. Preparation of Dye Precursor-containing Microcapsule Dispersion Solution (1)

"Dye precursor 20" (4.2 g) in the aforementioned specific example was dissolved in ethyl acetate (18.4 g). The resultant solution and TAKENATE D-110N (manufactured by Takeda Chemical Industries, Ltd.) (14 g) used as the material for the capsule wall were mixed, to thereby obtain a solution. Next, a 6% aqueous phthalated gelatin solution (70 g), and a 10% aqueous sodium dodecylbenzenesulfonate solution (0.34 g) were added to the solution. The resultant mixture was emulsified for 10 minutes at a rotational speed of 10,000 r.p.m by using a homogenizer (manufactured by Nihon Seiki Co., Ltd.). The resultant emulsion, water (54 g), and tetraethylenepentamine (0.62 g) were stirred and heated for three hours at a temperature of 65° C., and then a dye precursor-containing microcapsule dispersion solution (1) that contains the 'dye precursor 20' was obtained. The mean particle diameter of the capsules was 0.5 μm.

1-b. Preparation of Dye Precursor-containing Microcapsule Dispersion Solution (2)

A dye precursor-containing microcapsule dispersion solution (2) having microcapsules whose mean particle diameter is 0.5 μm was prepared in the same manner as in the above "1-a. preparation of dye precursor-containing microcapsule dispersion solution (1)" except that the "dye precursor 20" of the specific example was replaced by the "dye precursor 7".

1-c. Preparation of Dye Precursor-containing Microcapsule Dispersion Solution (3)

A dye precursor-containing microcapsule dispersion solution (3) was prepared in the same manner as in the above "1-b. preparation of dye precursor-containing microcapsule dispersion solution (2)" except that stirring conditions were changed into those which produced microcapsules with a mean particle diameter of 4 μm.

1-d. Preparation of Dye Precursor-containing Microcapsule Dispersion Solution (4)

A dye precursor-containing microcapsule dispersion solution (4) having microcapsules whose mean particle diameter is 0.5 μm was prepared in the same manner as the above "1-a. preparation of dye precursor-containing microcapsule dispersion solution (1)" except that the "dye precursor 20" in the examples was replaced by "dye precursor 8".

1-e. Preparation of Dye Precursor-containing Microcapsule Dispersion Solution (5)

A "dye precursor 9" (4.2 g) was dissolved in ethyl acetate (18.4 g). To the obtained solution were added a dye represented by the following structural formula (1) (0.05 g), an organic boron compound represented by the following structural formula (m) (0.4 g) which are photopolymerization initiators, pentaerythritol tetramethacrylate as a polymerizable compound (3 g), tricresyl phosphate (2 g), and TAKENATE D-110N (manufactured by Takeda Chemical Industries, Ltd.) (14 g) used as a material for the capsule. The obtained solution, a 6% aqueous phthalated gelatin solution (70 g), and a 10% aqueous sodium dodecylbenzenesulfonate solution (0.34 g) were mixed. The resultant mixture was emulsified by using the homogenizer (manufactured by Nihon Seiki Co., Ltd.) for 10 minutes at a rotational speed of 10,000 r.p.m. To the resultant emulsion were added water (54 g) and tetraethylenepentamine (0.62 g). The resultant mixture was stirred and heated for three hours at a temperature of 65° C. to thereby obtain a dye precursor-containing microcapsule dispersion solution (5) which has microcapsules whose mean particle diameter is 4 μm and which contain the photopolymerization initiator, the polymerizable compound, and an oil as core materials, together with the "dye precursor 9".

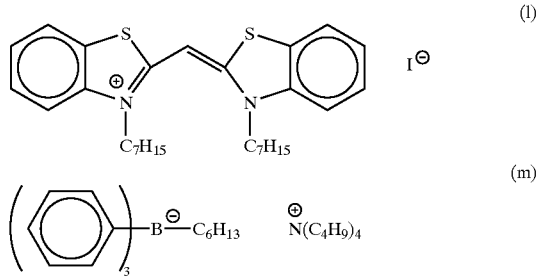

1-f. Preparation of Dye Precursor-containing Microcapsule Dispersion Solution (6)

A dye precursor-containing microcapsule dispersion solution (6) having microcapsules whose mean particle diameter is 0.5 μm was prepared in the same manner as in the above "1-a. Preparation of dye precursor-containing microcapsule dispersion solution (1)" except that the "dye precursor 20" of the specific example was replaced by a "dye precursor 25".

1-g. Preparation of Dye Precursor-containine Microcapsule Dispersion Solution for Comparison (H1)

A dye precursor-containing microcapsule dispersion solution for comparison (H1) having microcapsules whose mean particle diameter is 0.5 μm was prepared in the same manner as in the above "1-a. Preparation of the dye precursor-containing microcapsule dispersion solution (1)" except that the "dye precursor 20" of the specific example was replaced by a dye precursor represented by the following structural formula H1. Structural formula H1:

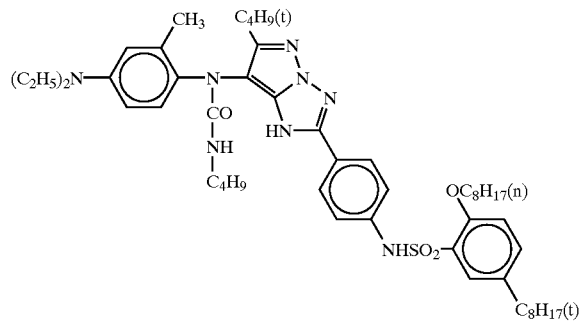

1-h. Preparation of Dye Precursor-containing Microcapsule Dispersion Solution for Comparison (H2)

A dye precursor-containing microcapsule dispersion solution for comparison (H2) having microcapsules whose mean particle diameter is 0.5 μm was prepared in the same manner in the above "1-a. Preparation of the dye precursor-containing microcapsule dispersion solution (1)" except that the "dye precursor 20" of the specific example was replaced by a dye precursor represented by the following structural formula H2.

Structural Formula H2:

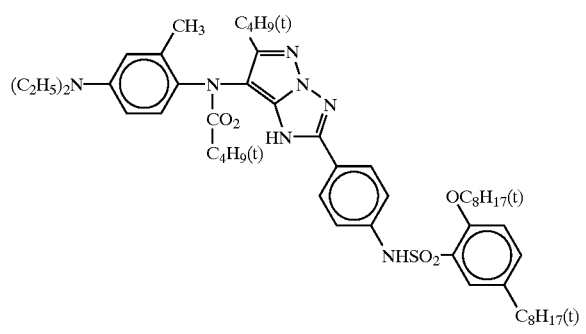

1-i. Preparation of Dye Precursor-containing Microcapsule Dispersion Solution for Comparison (H3)

A dye precursor-containing microcapsule dispersion solution for comparison (H3) having microcapsules whose mean particle diameter is 0.5 μm was prepared in the same manner as in the above "1-a. Preparation of the dye precursor-containing microcapsule dispersion solution (1)" except that the "dye precursor 20" of the specific example was replaced by a dye precursor represented by the following structural formula H3.

Structural Formula H3:

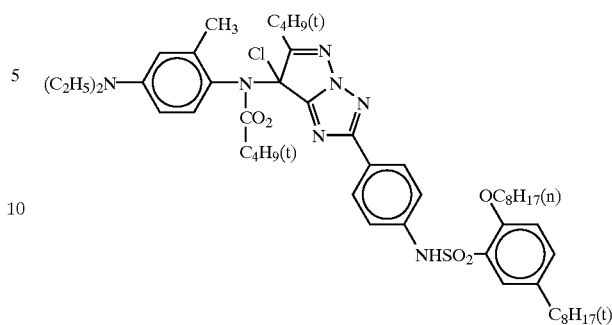

2. Preparation of Base Emulsion 2-a. Preparation of Base Emulsion (1)

N-methyloctadecylamine (2.4 g), a sulfonamide compound (1) (1.2 g) shown below, and a sulfonamide compound (2) (1.2 g) shown below were dissolved in isopropyl acetate (20.1 g). The obtained solution, a 10% aqueous gelatin solution (37.1 g), and a 10% aqueous sodium dodecylbenzenesulfonate solution (1.35 g) were mixed. The resultant mixture was emulsified for 5 minutes at a rotational speed of 15,000 r.p.m by using the homogenizer. The obtained emulsion was stirred for 3 hours at a temperature of 40° C., and isopropyl acetate was allowed to evaporate to thereby prepare a base emulsion (1).

Sulfonamide Compound (1):

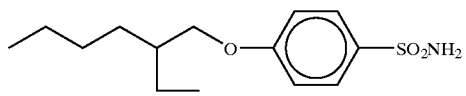

Sulfonamide Compound (2):

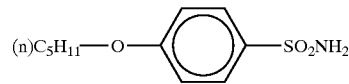

2-b. Preparation of Base Emulsion (2)

Ilgacure 819 (0.3 g) as the photopolymerization initiator, a compound represented by the following structural formula (a) used as the base serving as the polymerizable compound (4.5 g), a compound represented by the following structural formula (b) (2 g), a compound represented by the following structural formula (c) (2 g), and 1,1,3-tris (2-methyl-4-hydroxy-5-t-butylphenyl) butane (2 g) were added to ethyl acetate (10.5 g). Further, to the obtained solution, tricresyl phosphate as the high boiling point solvent (0.48 g), diethyl maleate (0.24 g), and Pyonine A 41C (manufactured by Takemoto Oil Co., Ltd.) (1.27 g) were added. The resultant solution was heated to thereby obtain a uniform mixture.

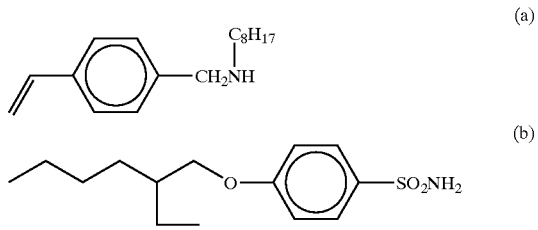

(c)

C₄H₉O—⟨phenyl⟩—OCH₂CONH₂

The aforementioned mixture was added to an 8% aqueous gelatin solution (#750 gelatin manufactured by Nitta Gelatin Co., Ltd.) (40 g). The obtained solution was emulsified for 5 minutes at a rotational speed of 10,000 r.p.m by using the homogenizer. The remaining ethylacetate was evaporated from the resultant emulsion to thereby prepare a base emulsion (2).

2-c. Preparation of Base Emulsion (3)

A base emulsion (3) was prepared in the same manner as the above-described preparation of the base emulsion (2) except that: the photopolymerization initiator was replaced by Ilgacure 907 (0.4 g), and the base serving as the photopolymerizable compound was replaced by a compound represented by the following structural formula (5 g) used as the base and trimethylolopropane trimethacrylate used as the polymerizable compound (4 g).

[Structure: bis(cyclohexyl-NH)C=N(CH₂)₆OCO—C(=CH₂)CH₃]

2-d. Preparation of Base Emulsion (4)

A base emulsion (4) was prepared in the same manner as the above-described preparation of the base emulsion (2) except that: the photopolymerization initiator was replaced by a dye represented by the following structural formula (d) (0.07 g) and an organic boron compound represented by the following structural formula (e) (0.5 g); the base serving as the polymerizable compound was replaced by a compound represented by the following structural formula (f) (5.5 g); and a polymerization aid represented by the following structural formula (g) (0.05 g) was added.

(d)

[Structure: cyanine dye with CH₃SO₂ groups, indole N-C₇H₁₅, with counterion CH₃-C₆H₄-SO₃⁻]

(e)

[Structure: (F-C₆H₄)₃B⁻—C₈H₁₃  N(C₄H₉)₄⁺]

(f)

(C₈H₁₇)₂N(CH₂)₂OCO—C(=CH₂)CH₃

(g)

[Structure: 4-diazo-naphthalenone with SO₃—C₆H₄—C₈H₁₇(t)]

2-e. Preparation of Base Emulsion (5)

A base emulsion (5) was prepared in the same manner as the above-described preparation of the base emulsion (2) except that: the photopolymerization initiator was replaced by a dye represented by the following structural formula (h) (0.06 g) and an organic boron compound represented by the following structural formula (i) (0.6 g); the base serving as the polymerizable compound was replaced by a compound represented by the following structural formula (j) (5.5 g); and pentaerythritol tetramethacrylate as the polymerizable compound (3 g) and a polymerization aid represented by the following structural formula (k) (0.05 g) were added.

(h)

[Structure: cyanine dye with CH₃SO₂ and SO₂CH₃ groups, indole N-C₇H₁₅, with counterion CH₃-C₆H₄-SO₃⁻]

(i)

[Structure: (F-C₆H₄)₃B⁻—CH(CH₃)-C₆H₅  N(C₄H₉)₄⁺]

(j)

(C₈H₁₇)₂N(CH₂)₂OCO—C(=CH₂)CH₃

(k)

[Structure: diphenyliodonium chloride, Ph₂I⁺ Cl⁻]

3. Preparation of Base Precursor Dispersion Solution

The following base precursor (1) (10 g), diphenylsulfone (10 g), a 5% aqueous phthalated gelatin solution (100 g), and a 2% aqueous solution of the following surfactant (1) (5.3 g) were mixed. The resultant solution was dispersed for 16 hours by using a ball mill, thus obtaining a base precursor dispersion solution.

Base Precursor (1):

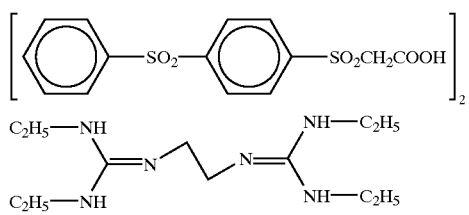

Surfactant (1):

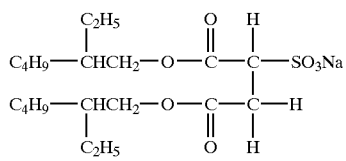

4. Preparation of Protective Layer Coating Solution

A 9% aqueous gelatin solution (113.5 g), the aforementioned surfactant (1) (2.6 g), and the following surfactant (2) (7.7 g) were mixed to thereby prepare a protective layer coating solution.

Surfactant (2)

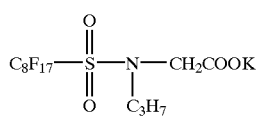

5. Preparation of Support

A white polyester base E68L (manufactured by Toray Industries., Inc.) having thickness of 100 μm was prepared.

EXAMPLE 1

The dye precursor-containing microcapsule dispersion solution (1) and the base emulsion (1) were mixed such that a concentration of the "dye precursor 20" of the specific example was $0.75 \times 10^{-3}$ mol/m$^2$, and a concentration of N-methyloctadecylamine was $1.5 \times 10^{-3}$ mol/m$^2$ to thereby prepare an image forming layer coating solution. The obtained coating solution was applied onto the support by using a coating bar and dried for 10 minutes at a temperature of 30° C. thus forming an image forming layer. The protective layer coating solution was applied to the image forming layer by using the coating bar so as to be 2.0 g/m$^2$ in a dried amount, and dried for 10 minutes at a temperature of 30° C., thus obtaining a heat-sensitive image forming material of Example 1.

EXAMPLE 2

A heat-sensitive image forming material of Example 2 was obtained in the same manner as in the Example 1 except that the dye precursor-containing microcapsule dispersion solution (1) in the Example 1 was replaced by the dye precursor-containing microcapsule dispersion solution (2) (whose concentration was adjusted on the basis of the "dye precursor 7").

EXAMPLE 3

A heat-sensitive image forming material in Example 3 was obtained in the same manner as in the Example 2 except that the base emulsion (1) in the Example 2 [described in a paragraph of the Example 1] was replaced by the base precursor dispersion solution (whose concentration was adjusted on the basis of the base precursor (1)).

(Image Forming Using the Image Forming Materials in the Examples 1 to 3 and Evaluation Thereof)

When each of the image forming materials thus obtained in the Examples 1 to 3 was heated imagewisely by using a hot plate for 15 seconds at a temperature of 120° C., the image forming material in the Example 1 formed a cyan color, and the image forming materials in the Examples 2 and 3 formed a magenta color. Density of the formed color of the image areas and background fogging in the non-image areas were measured by Macbeth reflection densitometer (RD918) using a cyan filter in the Example 1 and using a magenta filter in the Examples 2 and 3.

After a day has passed in a state in which each image forming material is placed under conditions of 40° C./90% relative humidity, background fogging at the non-image areas was measured in the same manner as described above. The results of these measurements are shown in Table 1 below:

TABLE 1

|  | immediately after coating | | one day later under conditions of 40° C./90% RH |
|---|---|---|---|
|  | density of image | fogging | fogging |
| Example 1 | 2.7 | 0.04 | 0.05 |
| Example 2 | 2.6 | 0.06 | 0.07 |
| Example 3 | 2.4 | 0.05 | 0.05 |

From the results of Table 1, it can be seen that the image forming material of the present invention is excellent in terms of density of the formed color, minimal background fogging, and storage stability.

COMPARATIVE EXAMPLE 1

An image forming material of Comparative Example 1 was obtained in the same manner as in the Example 1 except that the base emulsion (1) was not mixed into the image forming layer coating solution.

COMPARATIVE EXAMPLE 2

An image forming material of Comparative Example 2 was obtained in the same manner as in the Example 2 except that the base emulsion (1) was not mixed into the image forming layer coating solution.

(Image Formation Test Using the Image Forming Materials in the Comparative Examples 1 and 2)

When the image forming materials obtained in the Comparative Examples 1 and 2 were heated for 15 seconds at a temperature of 120° C. by using the hot plate, they did not form color. When they were heated further for 15 seconds at a temperature of 150° C., they did not form color. The results of measuring densities of the image forming materials in the Comparative Examples 1 and 2 before and after the above-described heating process by using the Macbeth reflection densitometer (RD918) are shown in Table 2 below:

TABLE 2

|  | fresh | 120° C., 15 sec. | 150° C., 15 sec. |
|---|---|---|---|
| Com. Example 1 | 0.04 | 0.04 | 0.04 |
| Com. Example 2 | 0.06 | 0.06 | 0.06 |

From the results of Table 2, it can be seen that even when the image forming materials which do not contain the base emulsion are heated to a predetermined temperature, they do not form color.

EXAMPLE 4

A pressure-sensitive image forming material of example 4 was obtained in the same manner as in the Example 1 except that the dye precursor-containing microcapsule dispersion solution (1) in the Example 1 was replaced by the dye precursor-containing microcapsule dispersion solution (3) (whose concentration was prepared on the basis of the "dye precursor 7").

The obtained image forming material was passed between pressurizing rollers whose linear load is 100 kg/cm. Image areas which were pressurized by the rollers formed a magenta color.

EXAMPLE 5

A pressure-sensitive image forming material of Example 5 was obtained in the same manner as in the Example 2 except that the base emulsion (1) in the Example 2 [described in the paragraph of the Example 1] was replaced by the base emulsion (2) (whose concentration was adjusted on the basis of the base serving as the polymerizable compound).

EXAMPLE 6

A pressure-sensitive image forming material of Example 6 was obtained in the same manner as in the Example 2 except that the base emulsion (1) in the Example 2 [described in a paragraph of the Example 1] was replaced by the base emulsion (3) (whose concentration was adjusted on the basis of the base).

(Image Formation Using the Image Forming Materials in Examples 5 and 6 and Evaluation Thereof)

The obtained image forming materials in the Examples 5 and 6 were irradiated with light for 30 seconds by using a xenon lamp (500 w) through a step wedge (density step: 0.15, the number of density steps: 1 to 15, and Fuji step guide P (manufactured by Fuji Photo Film Co., Ltd.)) by using a vacuum sintering apparatus to thereby form the latent image (latent image forming process). Thereafter, the entire surface of the image forming layer of the image forming material on which the latent image was formed was heated at a temperature of 120° C. for 15 seconds with a hot plate (developing process).

Portions of the exposed portion where light intensity was high did not form color, and density of the formed color was reduced at portions of the exposure portion where the light intensity was low. Among steps in which color formation did not take place, the step number of the step wedge (clear step number) corresponding to the step with the minimum exposure amount was determined. As for the clear step number, the higher the step number, the higher the sensitivity. The results of the clear step number and the measurement results of saturation densities ($D_{max}$) of the non-exposure portion (measured by a Macbeth reflection densitometer (RD918)) are shown in Table 3 as follows:

TABLE 3

|  | clear step number | $D_{max}$ |
|---|---|---|
| Example 5 | 10 | 2.1 |
| Example 6 | 9 | 2.0 |

COMPARATIVE EXAMPLE 3

When the image forming material of the Example 6 was heated for 15 seconds at a temperature of 120° C. without exposure, the entire surface of the image forming layer of the image forming material formed color. It is demonstrated that imagewise exposure is needed before the entire surface of the image forming layer is heated.

EXAMPLE 7

An image forming material of Example 7 was obtained in the same manner as in the Example 1 except that the dye precursor-containing microcapsule dispersion solution (1) in the Example 1 was replaced by the dye precursor-containing microcapsule dispersion solution (4) (whose concentration was adjusted on the basis of the "dye precursor 8"), and the base emulsion (1) was replaced by the base emulsion (4) (whose concentration was adjusted on the basis of the base serving as the photopolymerizable compound).

EXAMPLE 8

An image forming material of Example 8 was obtained in the same manner as in the Example 1 except that the dye precursor-containing microcapsule dispersion solution (1) in the Example 1 was replaced by the dye precursor-containing microcapsule dispersion solution (4) (whose concentration was adjusted on the basis of the "dye precursor 8"), and the base emulsion (1) was replaced by the base emulsion (5) (whose concentration was adjusted on the basis of the base serving as the photopolymerizable compound).

(Image Formation Using the Image Forming Materials of the Examples 7 and 8 and Evaluation Thereof)

A 650 nm semiconductor laser was used for the image forming material in the Example 7 and a 532 nm solid laser was used for the image forming material in the Example 8, to change image scanning speed so that maximum irradiation energy was 15 mJ/cm$^2$, thereby changing irradiation energy. Accordingly, these image forming layers were exposed in a step wedge form, thereby forming a latent image (latent image forming process).

When the entire surface of the image forming layer of each of the image forming materials having latent images formed thereon in the above-described manner was heated for 15 seconds at a temperature of 120° C. by using the hot plate, they clearly formed a magenta color so that images in a step wedge form were obtained (developing process).

The entire surface of each image forming layer on which an image is formed in the Examples 7 and 8, was irradiated with light for 30 seconds on a sharkasten with high intensity of 58000 lux. Accordingly, since the entire surface of an image was fixed on the layer, and a dye which is used as the photopolymerization initiator decomposes and becomes colorless, an image in which background portions of the non-image areas have higher whiteness was obtained (fixation process).

Saturation densities ($D_{max}$) of the image areas and fogging ($D_{min}$) of the non-image areas (background portions), of the obtained fixed image were measured by the Macbeth reflection densitometer (RD918). Difference between irradiation energy of a specific step in the above-described latent image forming process and irradiation energy used in the fixation process until background portions of each image forming material was formed ('irradiation energy used in the fixation process'-'irradiation energy of the aforementioned step in the latent forming process') was measured and computed to thereby become an index of sensitivity. As for the index of sensitivity, the smaller the value, the higher the sensitivity. The results of sensitivity, $D_{max}$, and $D_{min}$ are shown in Table 4 below:

TABLE 4

|  | sensitivity (mJ/cm$^2$) | $D_{max}$ | $D_{min}$ (background fogging) |
| --- | --- | --- | --- |
| Example 7 | 1.5 | 1.8 | 0.06 |
| Example 8 | 1.2 | 1.7 | 0.07 |

Further, the obtained image of each image forming material was irradiated with light whose irradiation intensity was 0.9W/m$^2$ for 48 hours by using a WEATHEROMEER CI65 (manufactured by ATLAS ELECTRIC DEVICES CO.) to thereby perform light-fastness evaluation. An evaluation index of light-fastness is a ratio of image density B after light irradiation for 48 hours to image density A when the image is fresh (B/A×100%). The results were 92% in the Example 7 and 91% in the Example 8. Thus, noticeable color fading was not seen in either example.

COMPARATIVE EXAMPLE 4

An image forming material of Comparative Example 4 was obtained in the same manner as in the Example 7 except that the dye precursor-containing microcapsule dispersion solution (4) in the Example 7 was replaced by the dye precursor-containing microcapsule dispersion solution for comparison (H1) (whose concentration was adjusted on the basis of the dye precursor represented by the structural formula H1).

COMPARATIVE EXAMPLE 5

An image forming material of Comparative Example 5 was obtained in the same manner as in the Example 7 except that the dye precursor-containing microcapsule dispersion solution (4) in the Example 7 was replaced by the dye precursor-containing microcapsule dispersion solution for comparison (H2) (whose concentration was adjusted on the basis of the dye precursor represented by the structural formula H2).

COMPARATIVE EXAMPLE 6

An image forming material of Comparative Example 6 was obtained in the same manner as in the Example 7 except that the dye precursor-containing microcapsule dispersion solution (4) in the Example 7 was replaced by the dye precursor-containing microcapsule dispersion solution for comparison (H3) (whose concentration was adjusted on the basis of the dye precursor represented by the aforementioned structural formula H3).
(Image Formation Test Using the Image Forming Materials in the Comparative Examples 4 to 6)

In the same manner as described in a paragraph, "Image formation using the image forming materials in the Examples 7 and 8 and evaluation thereof", operations of the latent forming process and the developing process were performed on the obtained image forming materials of the Comparative Examples 4 to 6. However, these image forming materials did not form color. Namely, even when a dye precursor which can form color through contact with a base was replaced by a dye precursor having a protective group which is not eliminated through contact with a base, color formation does not take place.

EXAMPLE 9

A pressure-sensitive image forming material of Example 9 was obtained in the same manner as in the Example 1 except that the dye precursor-containing microcapsule dispersion solution (1) in the Example (1) was replaced by the dye precursor-containing microcapsule dispersion solution (5) (whose concentration was adjusted on the basis of the "dye precursor 9").

In the same manner as (the latent forming process) explained in the paragraph, "Image formation using the image forming materials in the Examples 5 and 6 and evaluation thereof", a latent image through xenon exposure was formed on the obtained pressure-sensitive image forming material of the Example 9. Next, the obtained image forming material having the latent image formed thereon was passed between pressurizing rollers whose linear load is 100 kg/cm and developed (developing process). At this time, microcapsules in portions where an exposure amount was large were not broken, while the microcapsules in portions where the exposure amount was small were broken. In this way, an image in a step wedge form in accordance with the latent image was formed.

Further, in the same manner as (the fixation process) explained in the paragraph, "Image formation using the image forming materials in the Examples 7 and 8 and evaluation thereof", a dye which is used as the photopolymerization initiator was bleached by exposing the entire surface of the image forming layer of each image forming material. As a result, an image having background portions whose whiteness is higher was obtained.

EXAMPLE 10

1) Preparation of Cyan Image-forming Layer Coating Solution

An image forming layer coating solution was prepared in the same manner as in the Example 1 except that, during preparation of the image forming layer coating solution as described in the Example 1, the dye precursor-containing microcapsule dispersion solution (1) was replaced by the dye precursor-containing microcapsule dispersion solution (6) (whose concentration was adjusted on the basis of the "dye precursor 25"), and the base emulsion (1) was replaced by the base emulsion (4) (whose concentration was adjusted on the basis of the base serving as the polymerizable compound) to thereby prepare a cyan image-forming layer coating solution.

2) Preparation of Magenta Image-forming Layer Coating Solution

The image forming layer coating solution prepared in the Example 8 was used as a magenta image-forming layer coating solution.

3) Preparation of Intermediate Layer Solution

A 15% aqueous gelatin solution (4.5 g), distilled water (4.5 g), and a 2% aqueous solution of the following surfactant (0.3 g) were mixed to thereby prepare an intermediate layer solution.

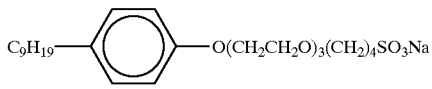

As is shown in FIG. 1, the cyan image-forming layer coating solution (layer A), the intermediate layer coating solution, and the magenta image-forming layer solution (layer B) were applied in this order to a support for printing paper formed by laminating polyethylene on high quality paper, and the result was then dried. Each of these coating solutions was applied in such an amount that after drying, solid matter was spread in the following amounts: each of the photosensitive recording layers, 6 g/m$^2$; and intermediate layer, 1.5 g/m$^2$. After drying, a protective layer was applied in an amount to become 2 g/m$^2$ when dry, and the result was dried, thus obtaining an image forming material of the Example 10.

A semiconductor laser light having a wavelength of 650 nm and a solid laser light having a wavelength of 532 nm were irradiated, from the protective layer side, onto the obtained image forming material of the Example 10 imagewisely so as to have a maximum irradiation energy which was 15 mJ/cm$^2$, thereby forming a latent image (latent image forming process). The entire surface of the image forming layer having the latent image formed thereon, of the image forming material was heated by the hot plate for 10 seconds at a temperature of 105° C. (developing process). Thereafter, the entire surface of the image forming layer was irradiated with light for 30 seconds on the high intensity sharkasten whose intensity was 58000 lux (fixation process). As a result, a color image in which clear color was formed, and which has background portions whose whiteness was higher was obtained. The obtained image was also excellent in light-fastness and heat-resistance.

What is claimed is:

1. A dye precursor for use with a base, the dye precursor comprising a compound represented by the following formula (1):

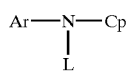
(1)

wherein Ar represents an aromatic ring or a heterocyclic ring, each of which may have a substituent; Cp represents a coupler residue; and L represents a protective group which can be eliminated by a base, and the compound forms a color when in contact with at least one base, wherein L is selected from the group consisting of the following structural formulas (5), (6), (7), (9) and (10):

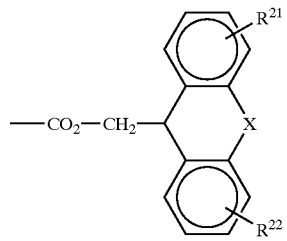
(5)

wherein X represents O, S, SO$_2$, or a single bond; and R$^{21}$ and R$^{22}$ represent a hydrogen atom, an alkyl group, an alkoxy group, an aryl group, or an electron attractive group;

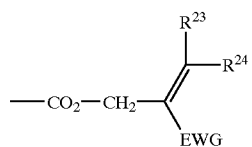
(6)

wherein R$^{23}$ and R$^{24}$ represent a hydrogen atom, an alkyl group, or an aryl group, EWG is an electron attractive group; and R$^{24}$ and EWG can form a ring in combination;

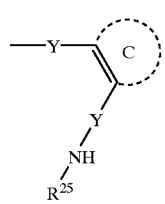
(7)

wherein Y represents CO or SO$_2$; R$^{25}$ represents a hydrogen atom, an alkyl group, an aryl group or a heterocyclic ring; and C represents an aryl group or a heterocyclic group;

—CH$_2$—NHSO$_2$R$^{27}$ (9)

wherein R$^{27}$ is the same as R$^{25}$ in structural formula (7);

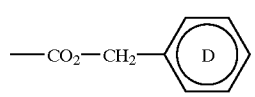
(10)

wherein

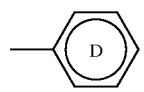

represents an aryl group with which a heterocyclic ring is condensed.

2. A dye precursor for use with a base, the dye precursor comprising a compound represented by the following formula (2)

(2)

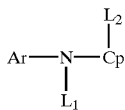

wherein Ar represents an aromatic ring or a heterocyclic ring, each of which may have a substituent; Cp represents a coupler residue; $L_1$ represents a protective group which can be eliminated by a base, and $L_2$ represents an elimination group or a protective group which is eliminated after $L_1$ is eliminated, and the compound forms a color when in contact with at least one base, wherein $L_1$ is selected from the group consisting of the following structural formulas (5), (6), (7), (9) and (10):

(5)

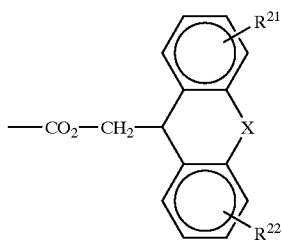

wherein X represents O, S, $SO_2$, or a single bond; and $R^{21}$ and $R^{22}$ represent a hydrogen atom, an alkyl group, an alkoxy group, an aryl group, or an electron attractive group;

(6)

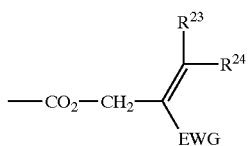

wherein $R^{23}$ and $R^{24}$ represent a hydrogen atom, an alkyl group, or an aryl group; EWG is an electron attractive group; and $R^{24}$ and EWG can form a ring in combination;

(7)

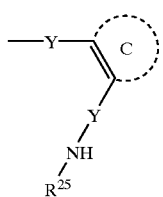

wherein Y represents CO or $SO_2$; $R^{25}$ represents a hydrogen atom, an alkyl group, an aryl group or a heterocyclic ring; and C represents an aryl group or a heterocyclic group;

 (9)

wherein $R^{27}$ is the same as $R^{25}$ in structural formula (7);

(10)

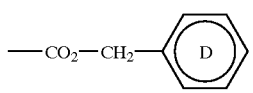

wherein

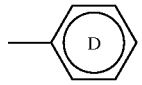

represents an aryl group with which a heterocyclic ring is condensed.

3. An image forming material comprising an image forming layer having a dye precursor which is represented by the following formula (1) or formula (2) and which forms a color when in contact with at least one base:

(1)

Ar—N—Cp
    |
    L wherein Ar represents an aromatic ring or a heterocyclic ring, each of which may have a substituent; Cp represents a coupler residue; and L represents a protective group which can be eliminated by a base;

(2)

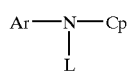

wherein Ar represents an aromatic ring or a heterocyclic ring, each of which may have a substituent; Cp represents a coupler residue; $L_1$ represents a protective group which can be eliminated by a base; and $L_2$ represents an elimination group or a protective group which is eliminated after $L_1$ is eliminated, wherein each of L and $L_1$ is selected from the group consisting of the following formulas (5), (6), (7), (9) and (10):

(5)

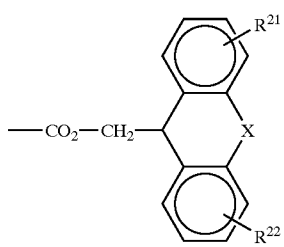

wherein X represents O, S, $SO_2$, or a single bond; and $R^{21}$ and $R^{22}$ represent a hydrogen atom, an alkyl group, an alkoxy group, an aryl group, or an electron attractive group;

(6)

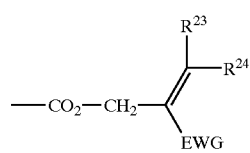

wherein $R^{23}$ and $R^{24}$ represent a hydrogen atom, an alkyl group, or an aryl group; EWG is an electron attractive group; and $R^{24}$ and EWG can form a ring in combination;

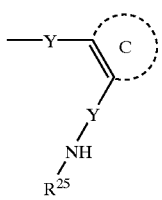
(7)

wherein Y represents CO or $SO_2$; $R^{25}$ represents a hydrogen atom, an alkyl group, an aryl group or a heterocyclic ring; and C represents an aryl group or a heterocyclic group;

 (9)

wherein $R^{27}$ is the same as $R^{25}$ in structural formula (7);

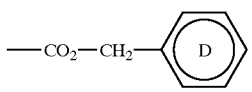 (10)

wherein

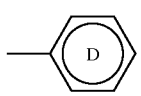

represents an aryl group with which a heterocyclic ring is condensed.

4. An image forming material comprising an image forming layer and a support, the image forming layer being disposed on the support and containing at least one type of each of a photopolymerization initiator, a dye precursor which can form color through contact with a base, a base or a base precursor, and a polymerizable compound, wherein said dye precursor is represented by the following formula (1) or formula (2):

Formula (1):

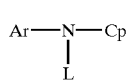 (1)

wherein Ar represents an aromatic ring or a heterocyclic ring, each of which may have a substituent; Cp represents a coupler residue; and L represents a protective group which can be eliminated by a base;

Formula (2):

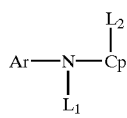 (2)

wherein Ar represents an aromatic ring or a heterocyclic ring, each of which may have a substituent; Cp represents a coupler residue; $L_1$ represents a protective group which can be eliminated by a base; and $L_2$ represents an elimination group or a protective group which is eliminated after $L_1$ is eliminated, wherein each of L and $L_1$ is selected from the group consisting of the following formulas (5), (6), (7), (9) and (10):

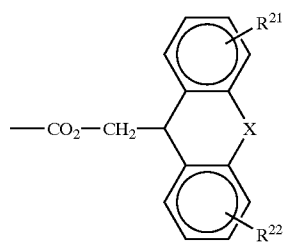 (5)

wherein X represents O, S, $SO_2$, or a single bond; and $R^{21}$ and $R^{22}$ represent a hydrogen atom, an alkyl group, an alkoxy group, an aryl group, or an electron attractive group;

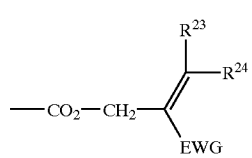 (6)

wherein $R^{23}$ and $R^{24}$ represent a hydrogen atom, an alkyl group, or an aryl group; EWG is an electron attractive group; and $R^{24}$ and EWG can form a ring in combination;

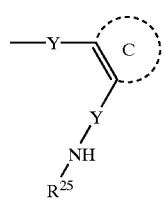 (7)

wherein Y represents CO or $SO_2$; $R^{25}$ represents a hydrogen atom, an alkyl group, an aryl group or a heterocyclic ring; and C represents an aryl group or a heterocyclic group;

 (9)

wherein $R^{27}$ is the same as $R^{25}$ in structural formula (7);

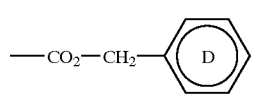 (10)

wherein

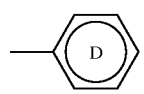

represents an aryl group with which a heterocyclic ring is condensed.

5. An image forming material according to claim 4, wherein said dye precursor is contained in microcapsules.

6. An image forming material according to claim 5, wherein a dye formed by said dye precursor, and said base or said base precursor is an azomethine dye.

7. An image forming material according to claim 6, wherein said base or said base precursor is a polymerizable compound.

8. An image forming material according to claim 5, wherein said base or said base precursor is a polymerizable compound.

9. An image forming material according to claim 4, wherein said photopolymerization initiator comprises a dye and an organic boron compound.

10. An image forming material according to claim 9, wherein said organic boron compound is represented by the following formula (3):

Formula (3):

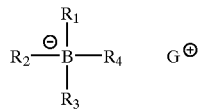

(3)

wherein $R_1$ to $R_4$ independently represent an alkyl group, an aryl group, a heterocyclic group, or $SiR_5R_6R_7$; $R_5$, $R_6$, and $R_7$ independently represent an alkyl group or an aryl group; and $G^+$ represents a group which is able to form a positive ion.

* * * * *